(12) United States Patent
Li et al.

(10) Patent No.: US 8,138,068 B2
(45) Date of Patent: Mar. 20, 2012

(54) METHOD TO FORM NANOPORE ARRAY

(75) Inventors: Zhengwen Li, Danbury, CT (US);
Chengwen Pei, Danbury, CT (US);
Frank Yang, Mahwah, NJ (US)

(73) Assignees: International Business Machines Corporation, Armonk, NY (US); Global Foundries, Grand Cayman (KY)

( * ) Notice: Subject to any disclaimer, the term of this patent is extended or adjusted under 35 U.S.C. 154(b) by 41 days.

(21) Appl. No.: 12/854,192

(22) Filed: Aug. 11, 2010

(65) Prior Publication Data

US 2012/0040512 A1 Feb. 16, 2012

(51) Int. Cl.
*H01L 21/20* (2006.01)
*H01L 21/36* (2006.01)
*H01L 21/4763* (2006.01)

(52) U.S. Cl. ............. 438/478; 438/619; 257/E21.577

(58) Field of Classification Search ......... 438/478, 438/479, 619, 629, 637, 640; 257/E21.577, 257/E21.573
See application file for complete search history.

(56) References Cited

U.S. PATENT DOCUMENTS

| | | | |
|---|---|---|---|
| 6,261,943 B1 * | 7/2001 | Grupp | 438/619 |
| 6,515,845 B1 | 2/2003 | Oh et al. | |
| 6,627,067 B1 * | 9/2003 | Branton et al. | 205/778 |
| 6,638,885 B1 | 10/2003 | McGrath et al. | |
| 6,960,298 B2 | 11/2005 | Krotz et al. | |
| 7,045,851 B2 | 5/2006 | Black et al. | |
| 7,098,393 B2 | 8/2006 | Fleurial et al. | |
| 7,217,562 B2 | 5/2007 | Cao et al. | |
| 7,223,894 B2 | 5/2007 | Chau et al. | |
| 7,248,771 B2 | 7/2007 | Schmidt et al. | |
| 7,250,544 B2 | 7/2007 | Chau et al. | |
| 7,274,078 B2 | 9/2007 | Jaiprakash et al. | |
| 7,444,053 B2 | 10/2008 | Schmidt et al. | |
| 7,582,490 B2 | 9/2009 | Golovchenko et al. | |
| 7,586,618 B2 | 9/2009 | Marks et al. | |
| 7,610,074 B2 | 10/2009 | Boppart et al. | |
| 7,615,926 B2 * | 11/2009 | Eden et al. | 313/582 |
| 7,623,908 B2 | 11/2009 | Boppart et al. | |
| 7,626,246 B2 * | 12/2009 | Lochtefeld et al. | 257/647 |
| 7,736,943 B2 * | 6/2010 | Tombler et al. | 438/100 |
| 7,833,832 B2 * | 11/2010 | Wood et al. | 438/109 |
| 7,906,284 B2 * | 3/2011 | Turner et al. | 435/6.12 |
| 2004/0043208 A1 * | 3/2004 | Fukutani et al. | 428/304.4 |
| 2004/0262770 A1 * | 12/2004 | Ozawa | 257/758 |
| 2007/0093009 A1 | 4/2007 | Baptist et al. | 438/176 |
| 2008/0203317 A1 * | 8/2008 | Platzgummer et al. | 250/396 R |
| 2008/0272396 A1 * | 11/2008 | Fournel et al. | 257/190 |
| 2009/0220561 A1 * | 9/2009 | Jin et al. | 424/423 |
| 2009/0235915 A1 * | 9/2009 | Doumanidis et al. | 126/263.01 |
| 2011/0210259 A1 * | 9/2011 | Elam et al. | 250/370.11 |

* cited by examiner

*Primary Examiner* — Walter L Lindsay, Jr.
(74) *Attorney, Agent, or Firm* — Scully, Scott, Murphy & Presser, P.C.; H. Daniel Schnurmann

(57) ABSTRACT

A method of forming nanopore is provided that includes forming a first structure on a substrate, and forming a second structure overlying the first structure. An intersecting portion of the first and the second structures is etched to provide an opening of nanopore dimensions. The substrate may be etched with a backside substrate etch to expose the nanopore opening.

20 Claims, 16 Drawing Sheets

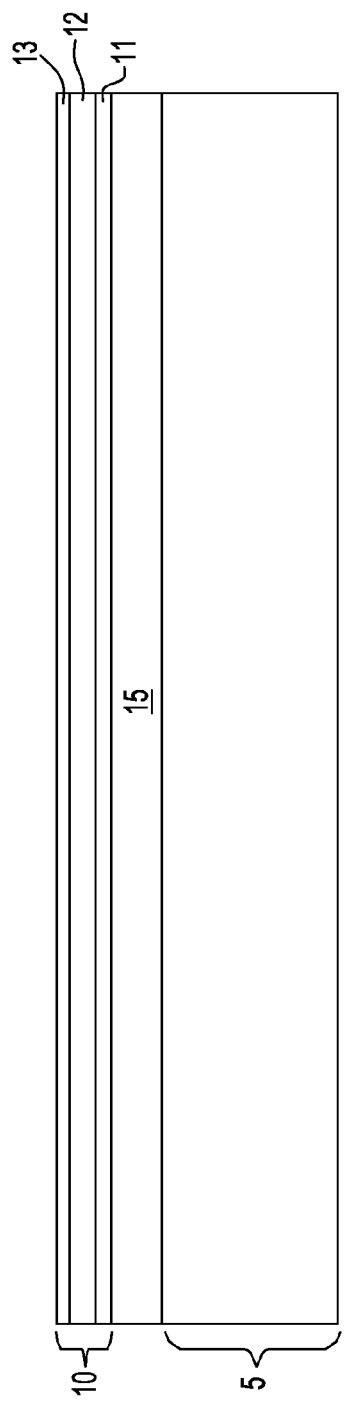
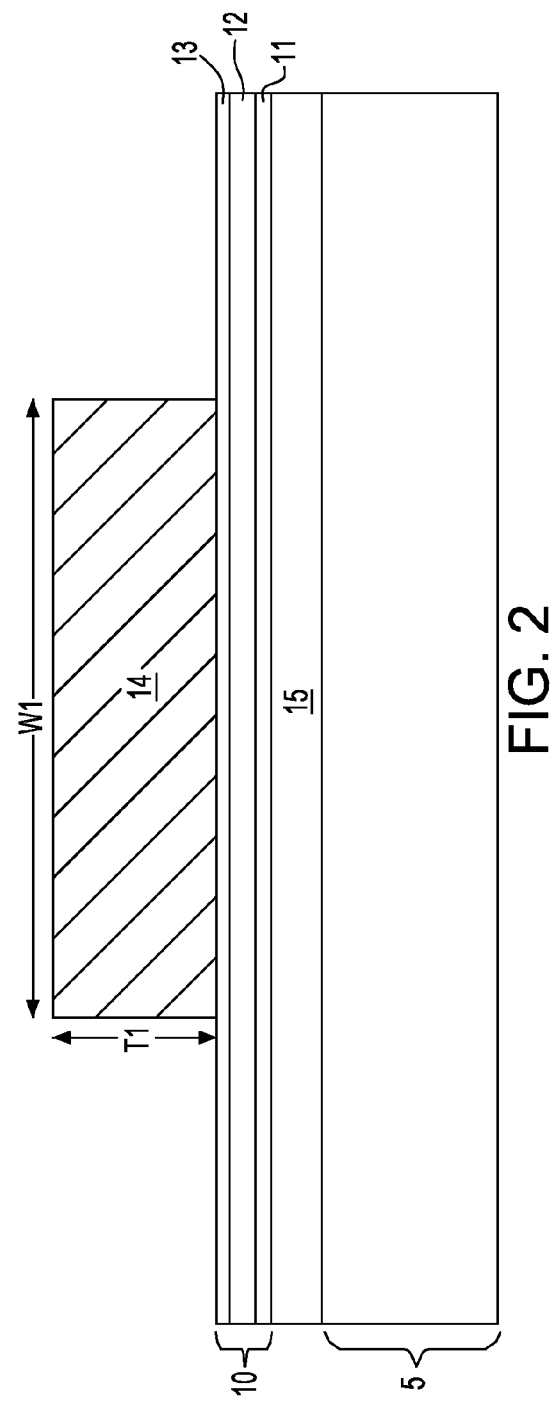

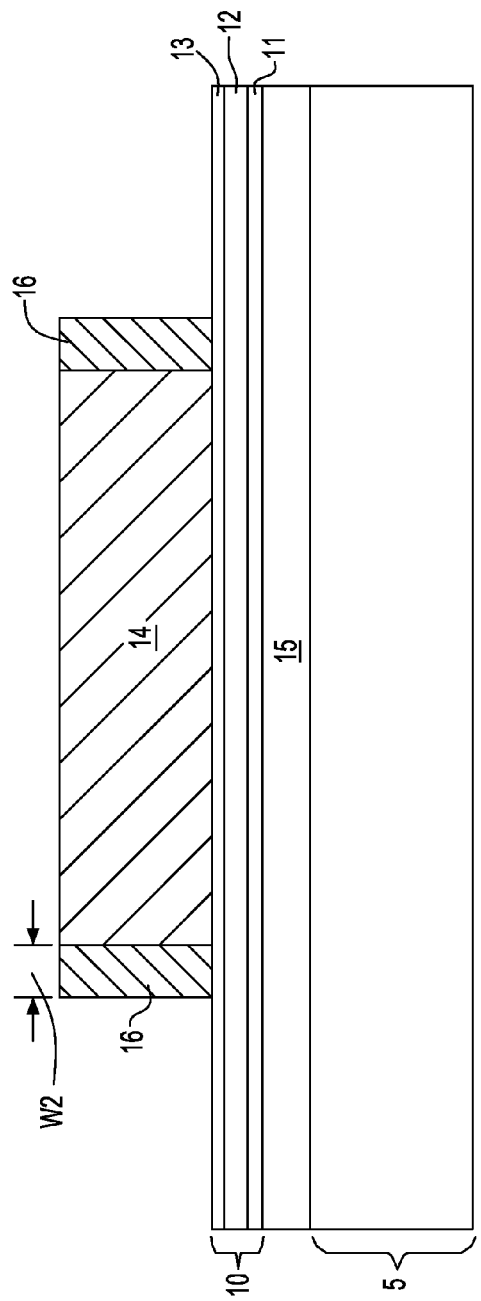
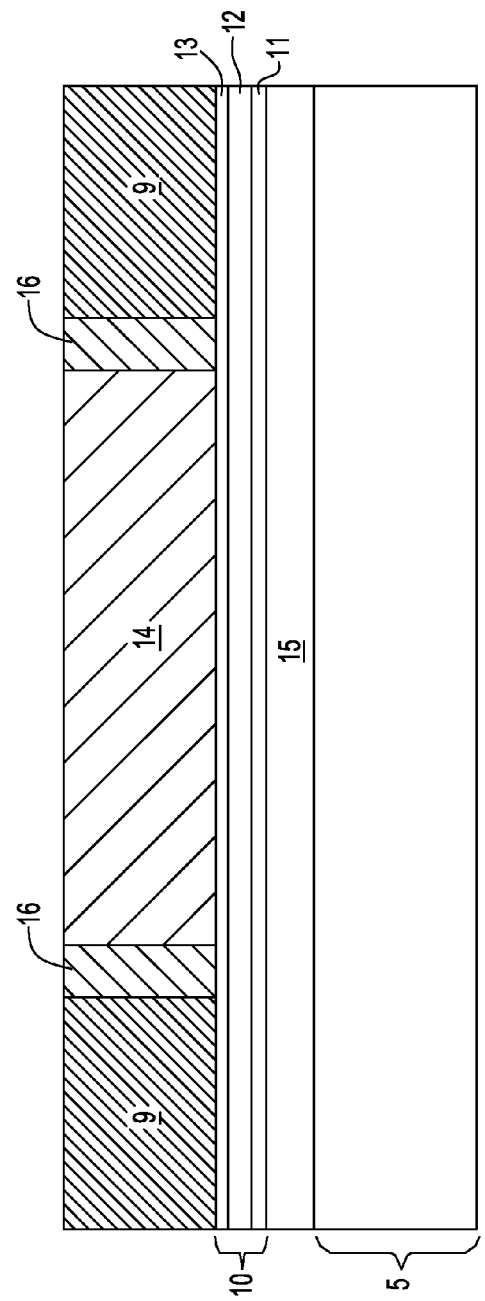

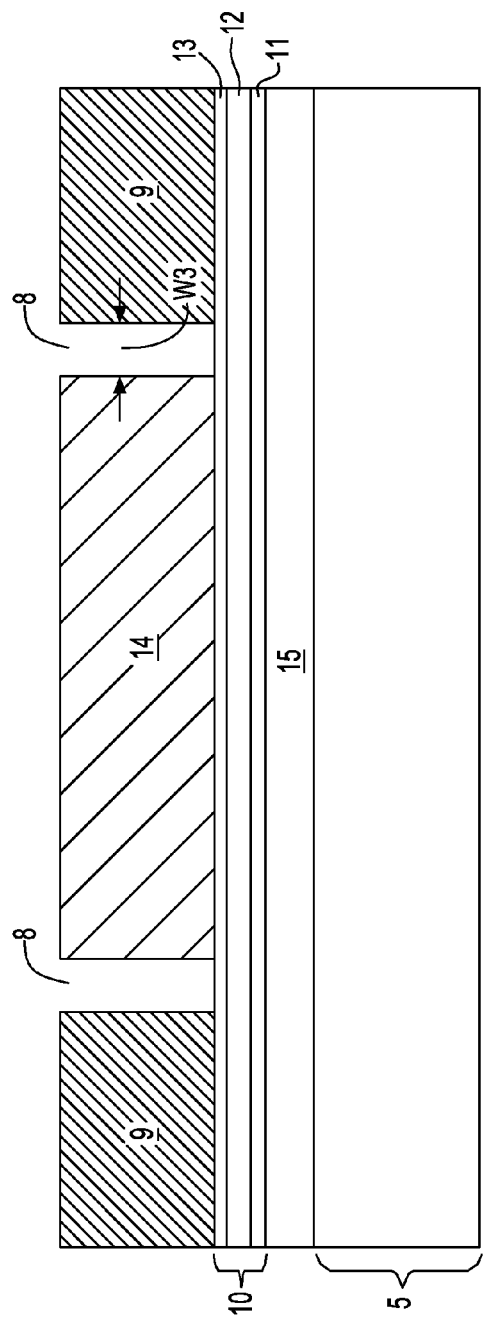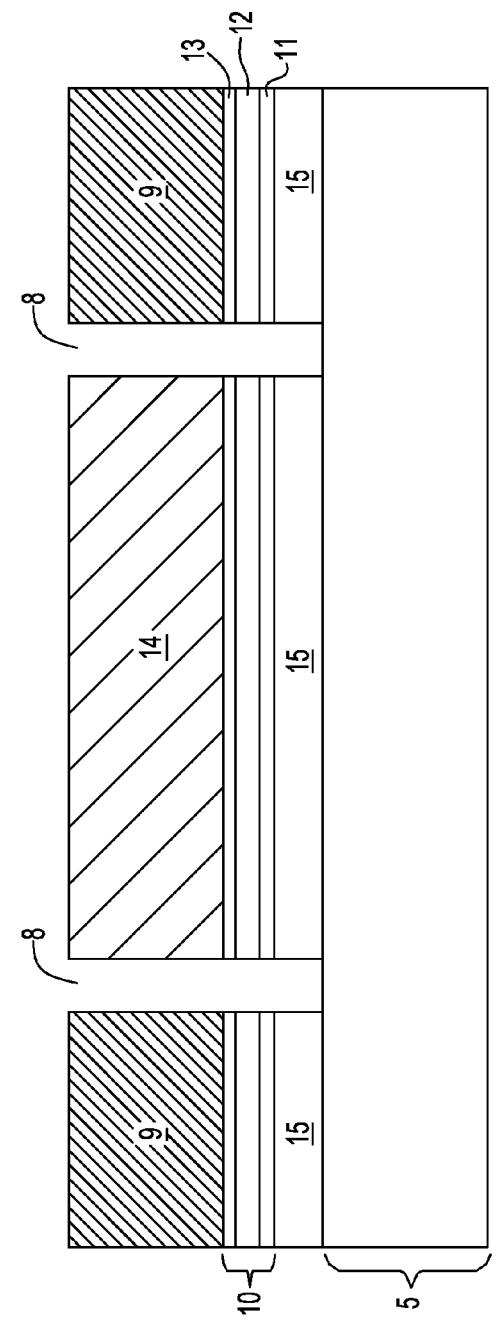
FIG. 5
FIG. 6

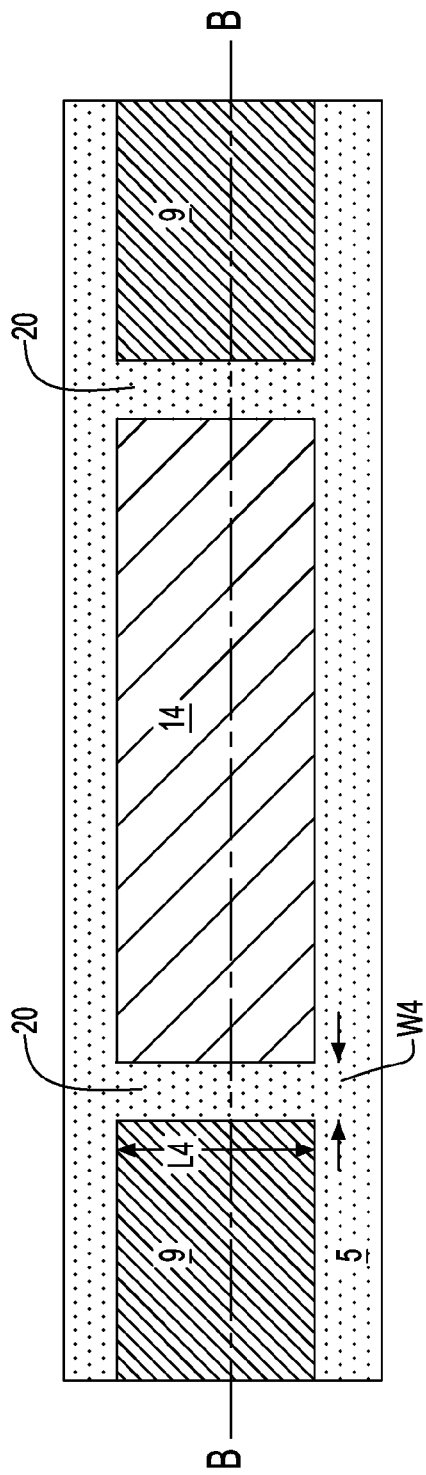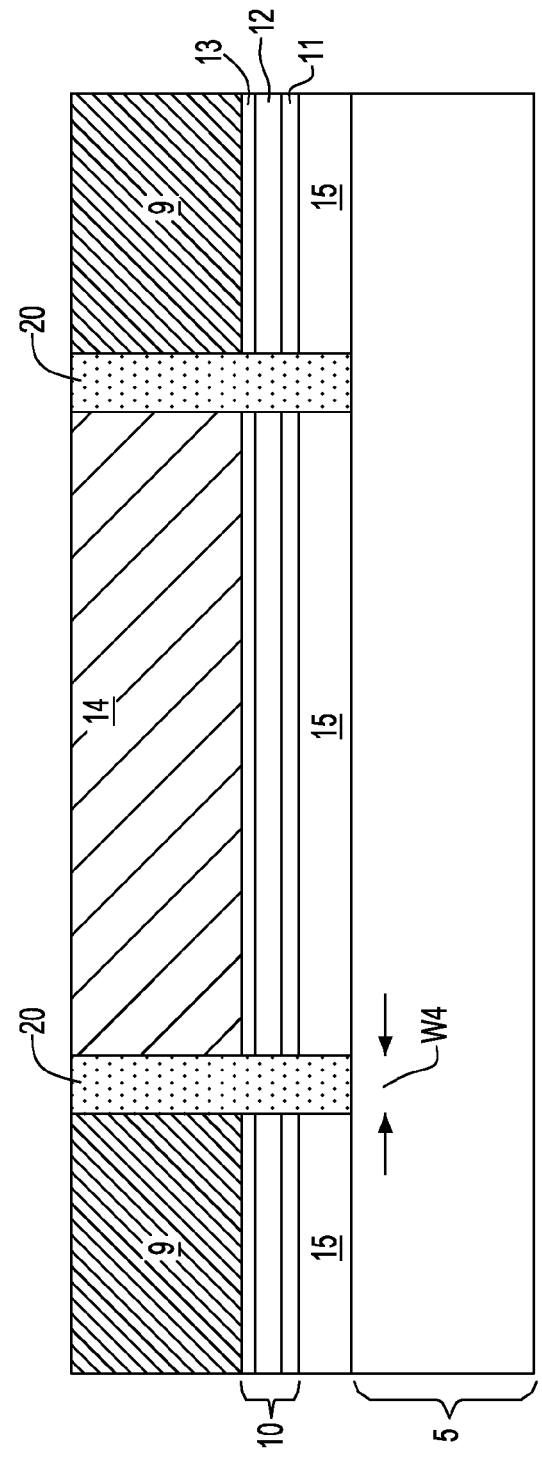
FIG. 7A
FIG. 7B

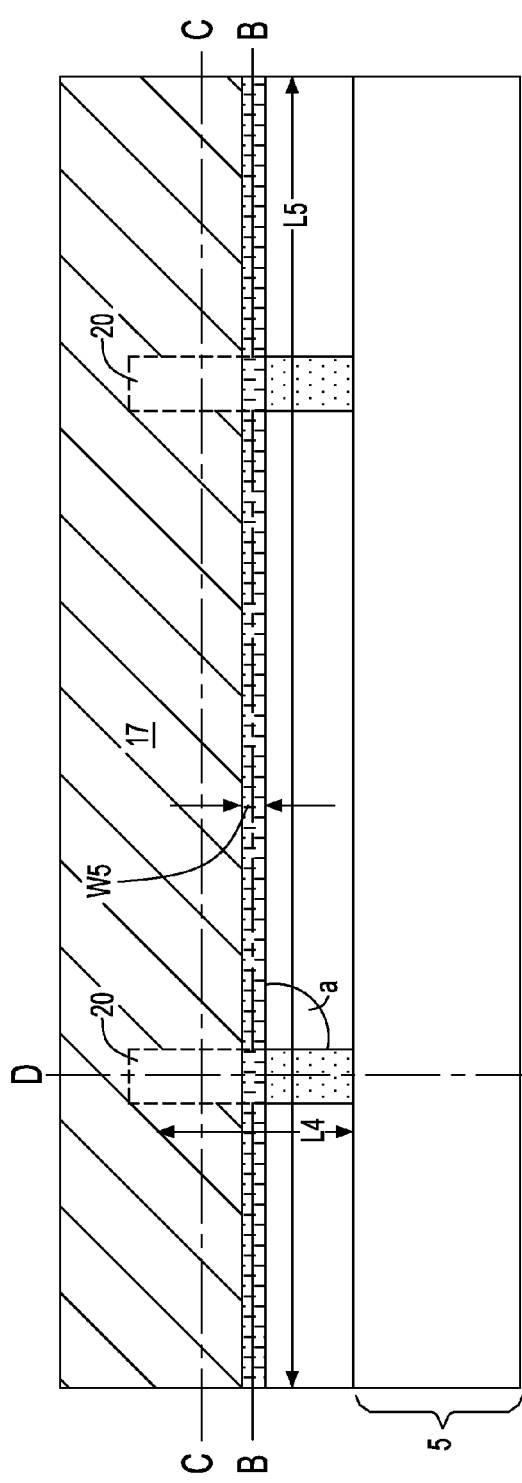
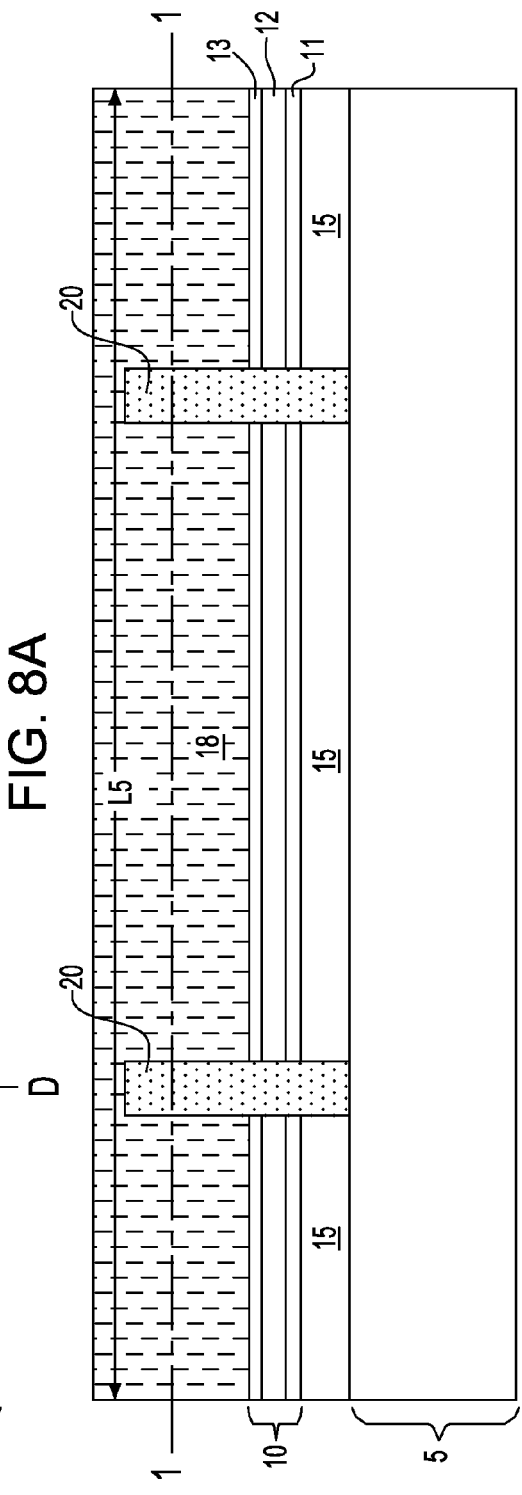
FIG. 8A
FIG. 8B

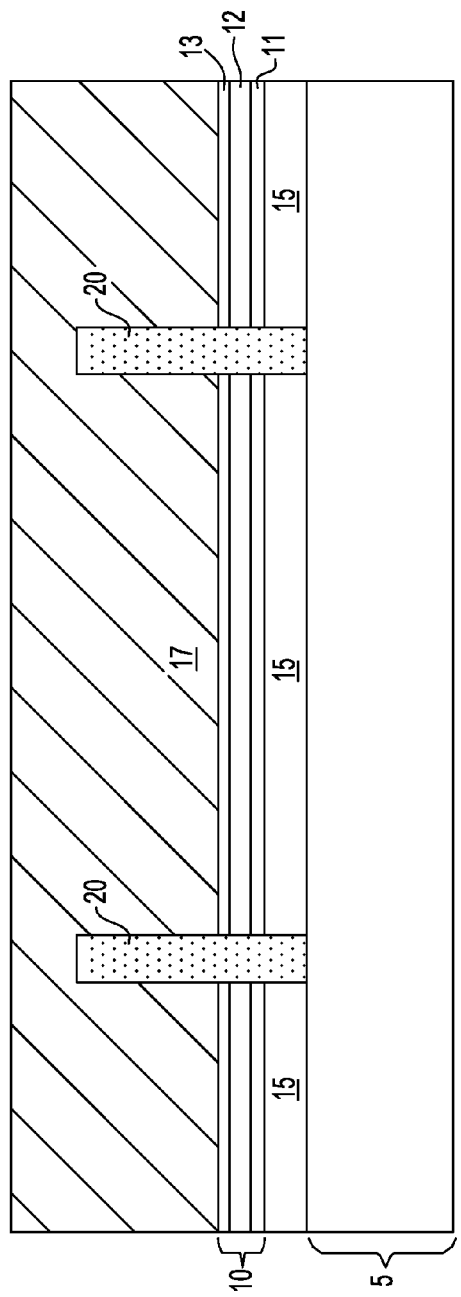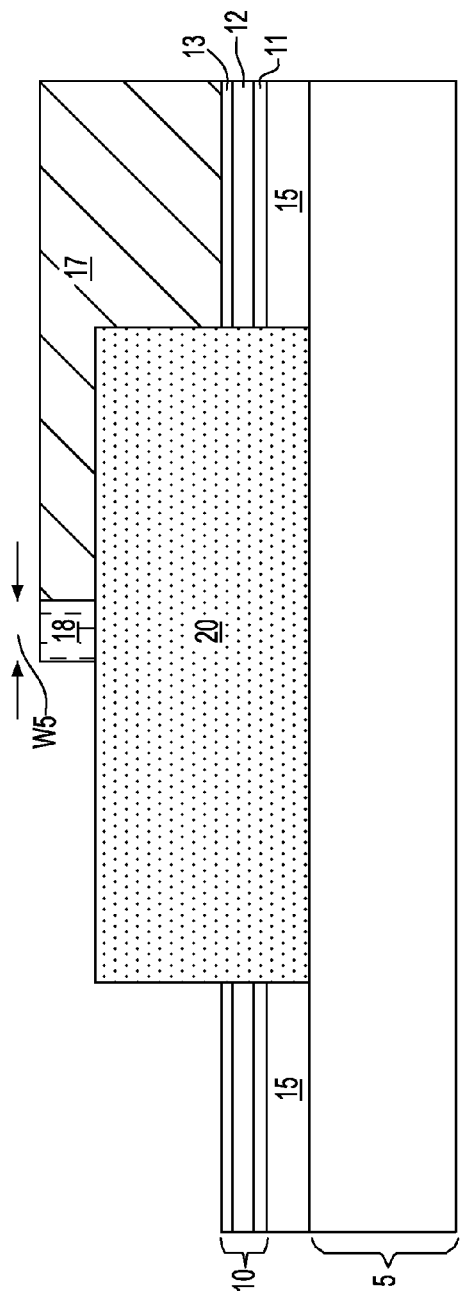

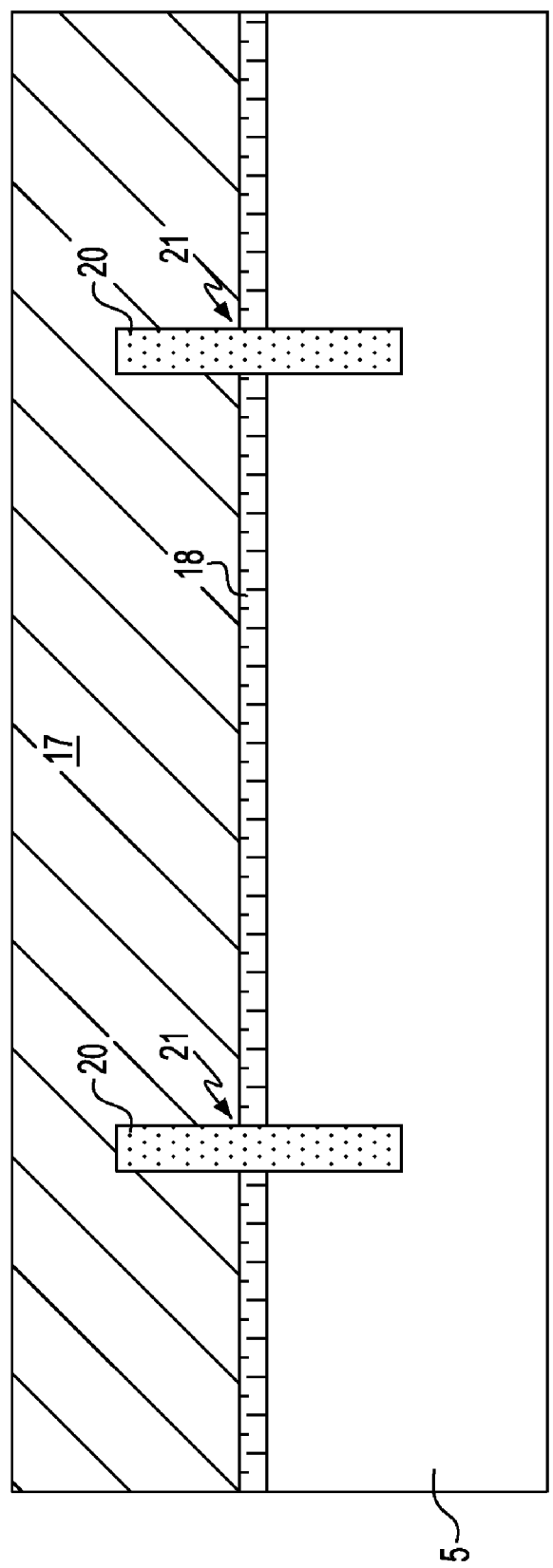

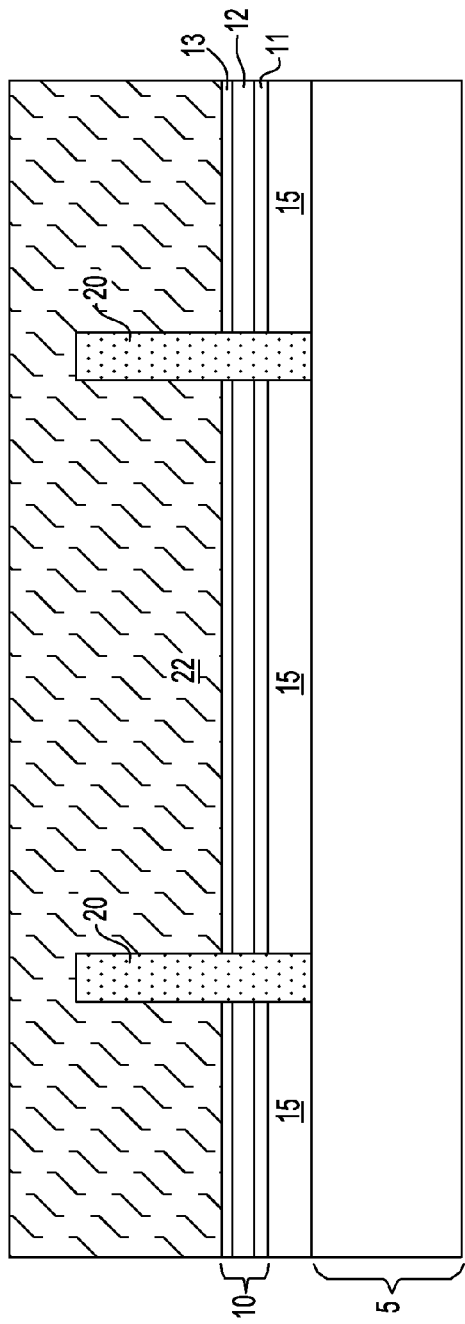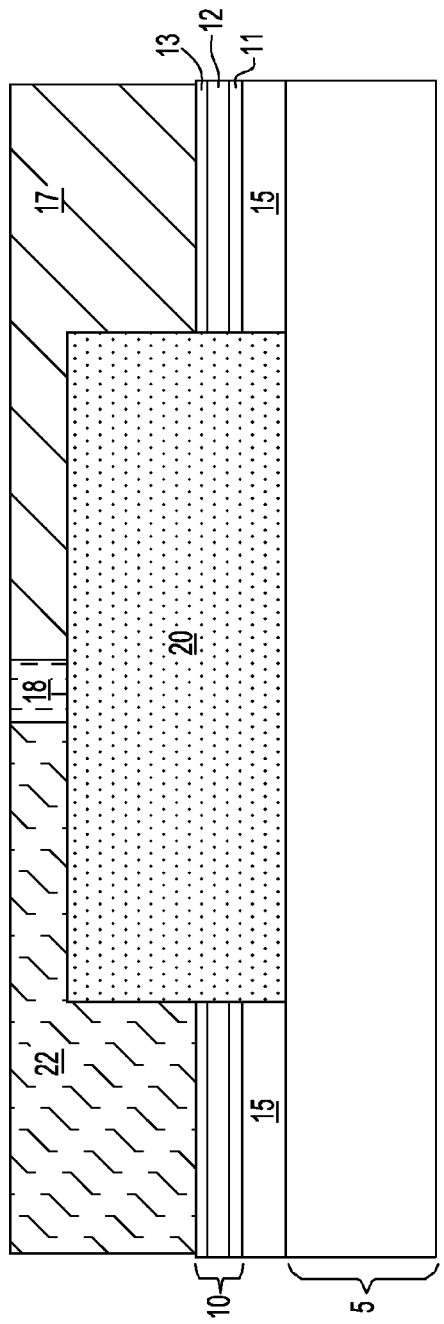

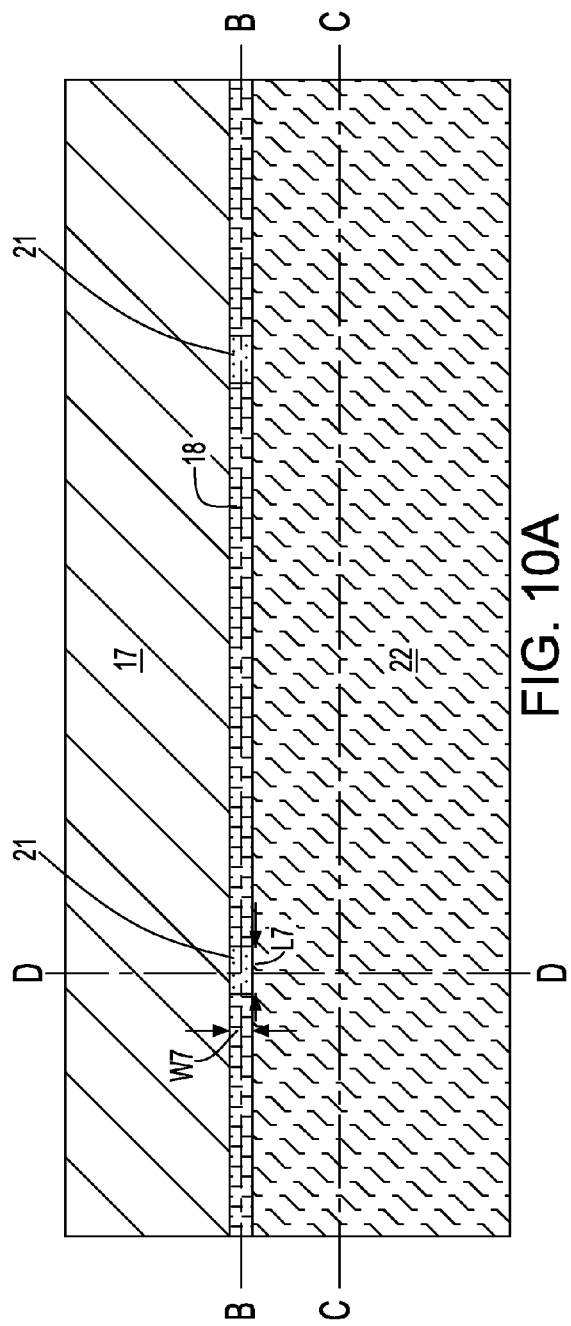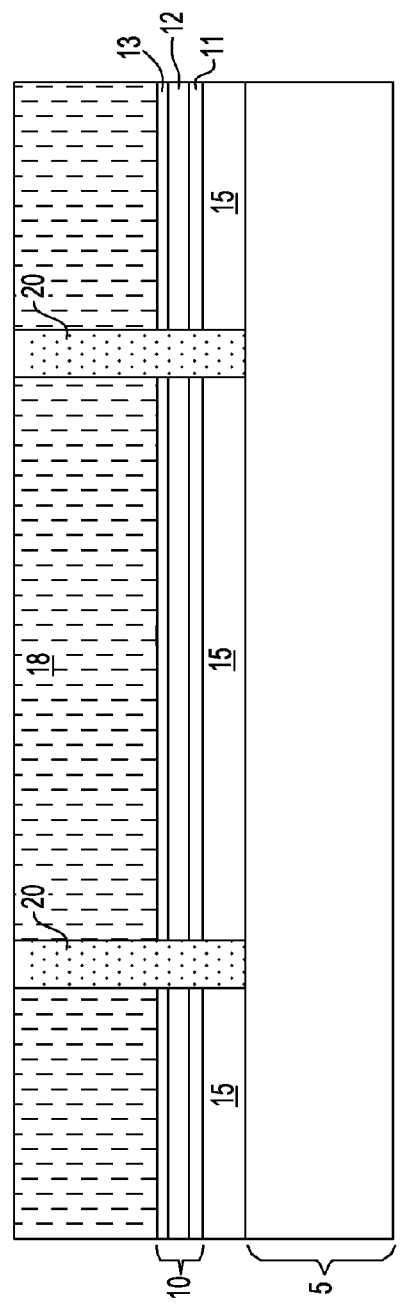

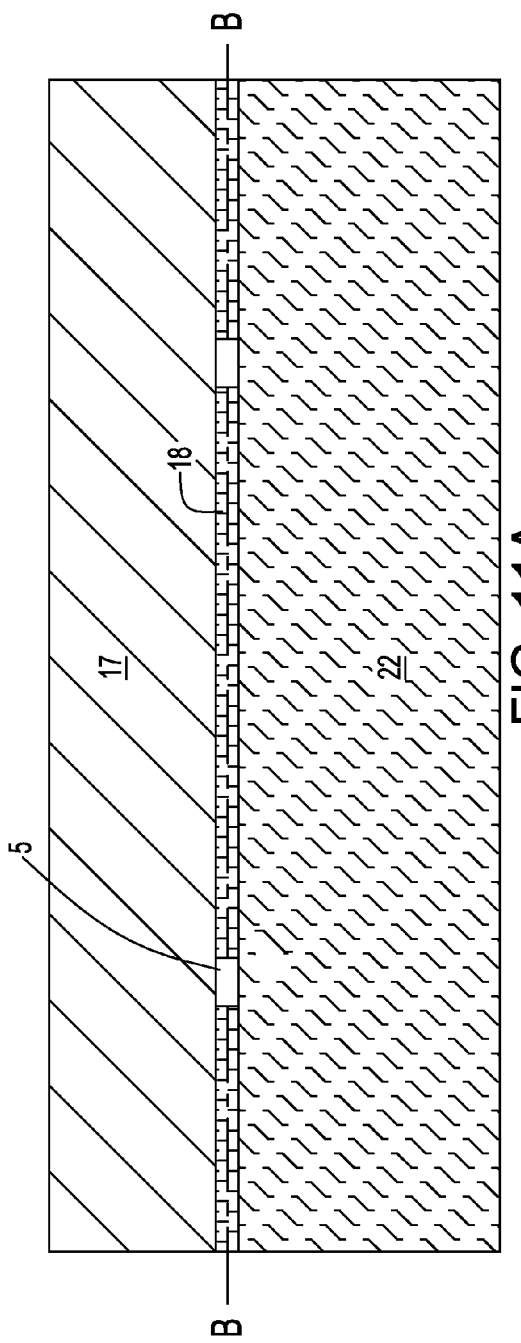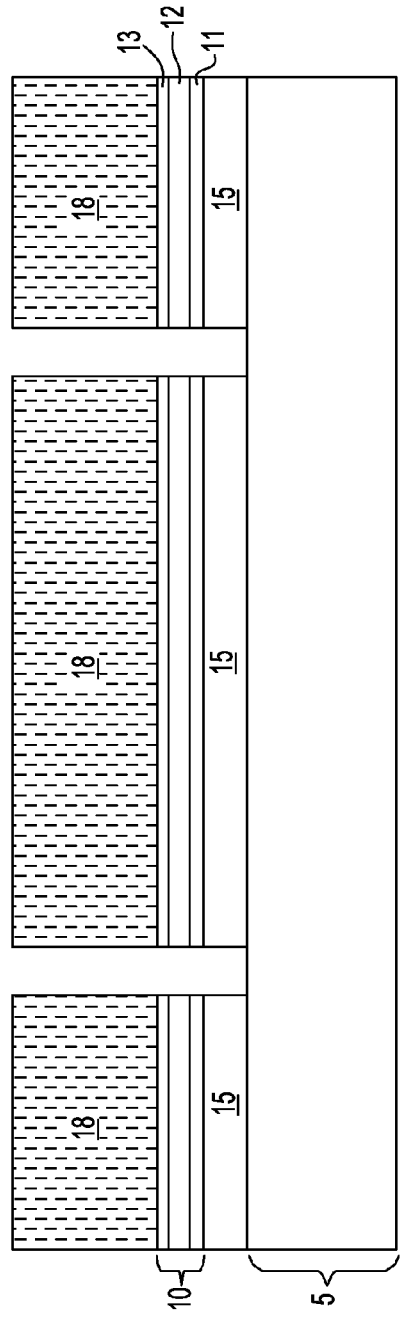

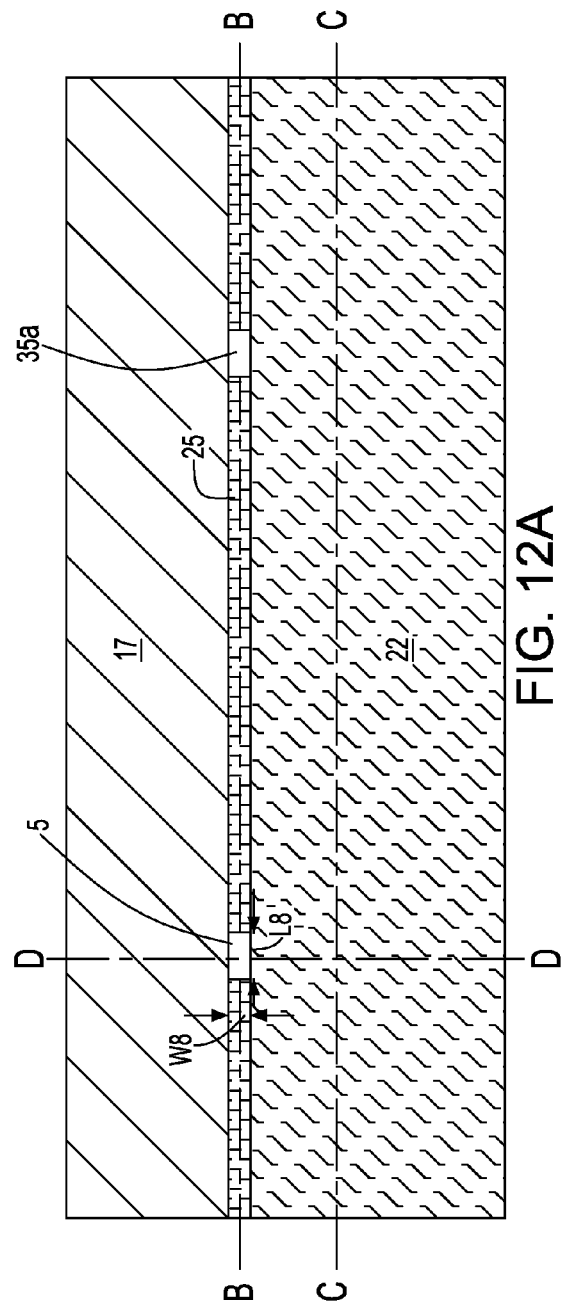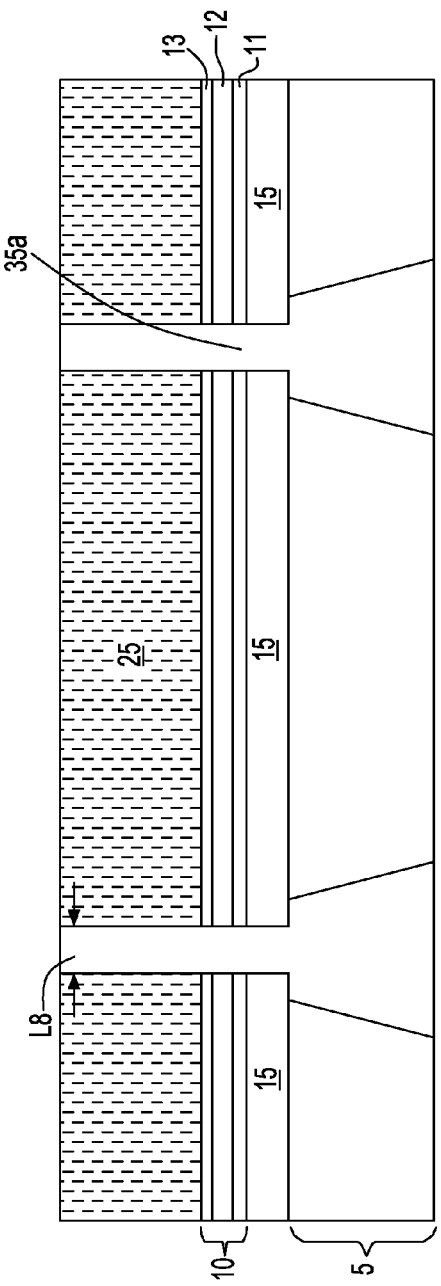

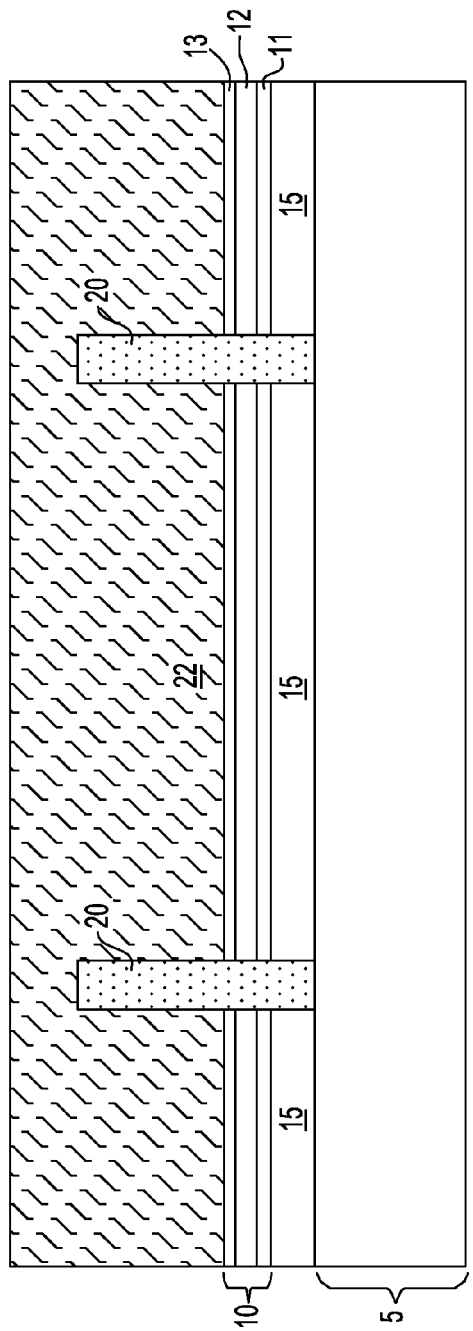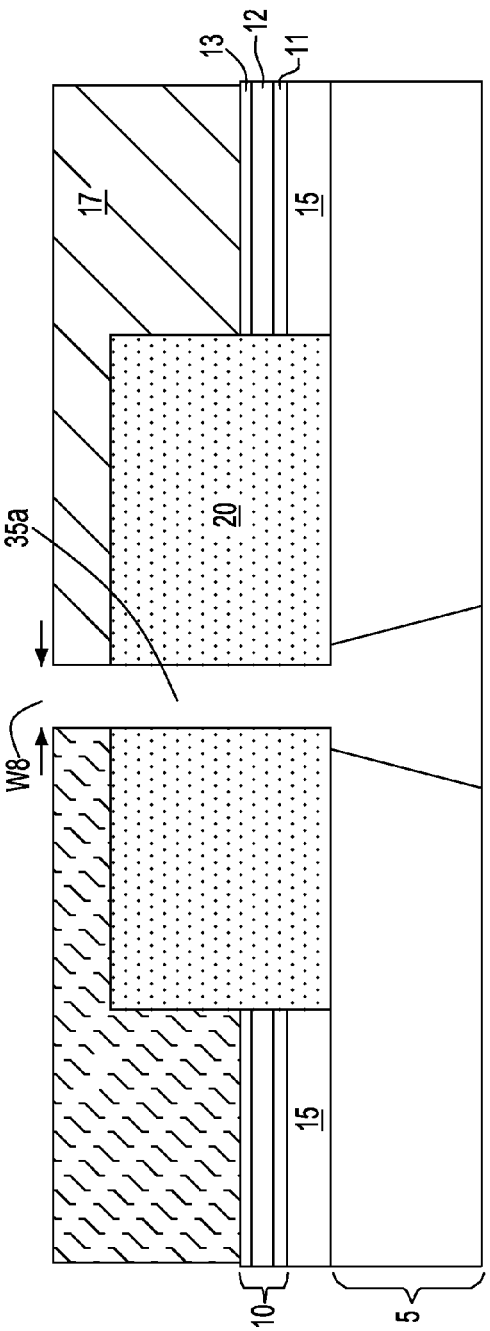

METHOD TO FORM NANOPORE ARRAY

BACKGROUND

The present disclosure relates to methods of forming structures including porosity, such as fluidic channels.

The use of pore containing materials, such as fluidic channels, is known for the treatment and observation of, research on, or even the culturing of living cells. For example, fluidic channels including pores are in some instances suitable for DNA sequencing, and molecular sensors. Pore containing materials are also suitable for water filtration. Porosified semiconductor materials are one type of material that may be utilized in the above applications.

SUMMARY

In one embodiment, a method of forming nanopores is provided that includes forming a first structure on a substrate. A second structure is also formed on the substrate, wherein the second structure overlaps an intersecting portion of the first structure. An etch mask is formed over the exposed portions of the first structure and the exposed portions of the substrate. A first etching process etches the second structure selective to the etch mask to expose the intersecting portion of the first structure. A remaining portion of the second structure is present on opposing sides of the intersecting portion of the first structure. A second etching process etches the exposed intersecting portion of the first structure selective to the etch mask and the remaining portion of the second structure to provide an opening to the substrate. The opening is extended through the substrate to provide a nanopore.

In another embodiment, the method of forming nanopores may begin with forming a first structure on the substrate. A first mask structure is formed on the substrate and over a first end portion of the first structure. A second mask structure is formed on the substrate adjacent and over a second end portion of the first structure. A second structure is formed between the first mask structure and the second mask structure. The second structure overlaps an intersecting portion of the first structure. The second structure is etched with an etch that is selective to the first mask structure, the second mask structure and the first structure to provide an exposed intersecting portion of the first structure. The exposed intersecting portion of the first structure is etched to provide an opening.

In yet another embodiment, the method of forming a nanopore includes forming a first sacrificial material on sidewalls of a first pedestal that is present on a substrate, and forming a first mask adjacent to the first sacrificial material. The first sacrificial material is removed to provide a first void between the first pedestal structure and the first mask. A first structure is formed by filling the first void. The first pedestal and the first hardmask are removed selective to the first structure.

A second pedestal is formed on the substrate, wherein the second pedestal overlaps a first end portion of the first structure. A second structure is formed on sidewalls of the second pedestal and on an intersecting portion of the first structure. A second mask is formed adjacent to the second structure. The second mask is present over a second end portion of the first structure.

The second structure is etched to expose the intersecting portion of the first structure, wherein a remaining portion of the second structure is present on opposing sides of the first structure. The exposed intersecting portion of the first structure is etched selective to the second structure, the second mask, and the second pedestal to provide a nanopore. The substrate is etched with a backside etch to expose the nanopore.

DESCRIPTION OF THE DRAWINGS

The following detailed description, given by way of example and not intended to limit the invention solely thereto, will best be appreciated in conjunction with the accompanying drawings, wherein like reference numerals denote like elements and parts, in which:

FIG. 1 is a side cross-sectional view depicting one embodiment of a substrate including a material stack present on the upper surface of the substrate, as used in accordance with the present disclosure.

FIG. 2 is a side cross-sectional view depicting forming a first pedestal on a substrate, in accordance with one embodiment of the present disclosure.

FIG. 3 is a side cross-sectional view depicting forming a first sacrificial material on sidewalls of the first pedestal, in accordance with one embodiment of the present disclosure.

FIG. 4 is a side cross-sectional view depicting forming a first mask adjacent to the first sacrificial material, in accordance with one embodiment of the present disclosure.

FIG. 5 is a side cross-sectional view depicting removing the first sacrificial material to provide a first void between the first pedestal structure and the first hardmask, in accordance with one embodiment of the present disclosure.

FIG. 6 is a side cross-sectional view depicting etching the material stack using the first void as an etch mask, in accordance with one embodiment of the present disclosure.

FIGS. 7A and 7B depict filling the first void to form a first structure having a first width of 5 nm or less and a first length of 5 nm or more, in accordance with one embodiment of the present disclosure. FIG. 7A is a top down planar view. FIG. 7B is a side cross sectional view along section line B-B as depicted in FIG. 7A.

FIGS. 8A-8E depict forming a second pedestal on the substrate, wherein the second pedestal is formed over a first end of the first structure, and forming a second structure on the sidewall of the second pedestal, wherein the second structure overlaps an intersecting portion of the first structure, in accordance with one embodiment of the present disclosure. FIG. 8A is a top down planar view. FIG. 8B is a side cross sectional view along section line B-B as depicted in FIG. 8A. FIG. 8C is a side cross sectional view along section line C-C as depicted in FIG. 8A. FIG. 8D is a side cross sectional view along section line D-D as depicted in FIG. 8A. FIG. 8E is a top down cross sectional view along section line 1-1 as depicted in FIG. 8B.

FIGS. 9A-9E depict forming a second mask adjacent to the second structure, in accordance with one embodiment of the present disclosure. FIG. 9A is a top down planar view. FIG. 9B is a side cross sectional view along section line B-B as depicted in FIG. 9A. FIG. 9C is a side cross sectional view along section line C-C as depicted in FIG. 9A. FIG. 9D is a side cross sectional view along section line D-D as depicted in FIG. 9A. FIG. 9E is a top down cross sectional view along section line 1-1 as depicted in FIG. 9B.

FIGS. 10A-10D depict etching the second structure to expose the intersecting portion of the first structure, in accordance with one embodiment of the present disclosure. FIG. 10A is a top down planar view. FIG. 10B is a side cross sectional view along section line B-B as depicted in FIG. 10A. FIG. 10C is a side cross sectional view along section line C-C as depicted in FIG. 10A. FIG. 10D is a side cross sectional view along section line D-D as depicted in FIG. 10A.

FIGS. 11A-11B depict etching the exposed intersecting portion of the first structure to provide an opening having a width of 5 nm or less and a length of 5 nm or less, in accordance with one embodiment of the present disclosure. FIG. 11A is a top down planar view. FIG. 11B is a side cross sectional view along section line B-B as depicted in FIG. 11A.

FIGS. 12A-12D depict etching the substrate, in accordance with one embodiment of the present disclosure. FIG. 12A is a top down planar view. FIG. 12B is a side cross sectional view along section line B-B as depicted in FIG. 12A. FIG. 12C is a side cross sectional view along section line C-C as depicted in FIG. 12A. FIG. 12D is a side cross sectional view along section line D-D as depicted in FIG. 12A.

DETAILED DESCRIPTION

Figure 9A:
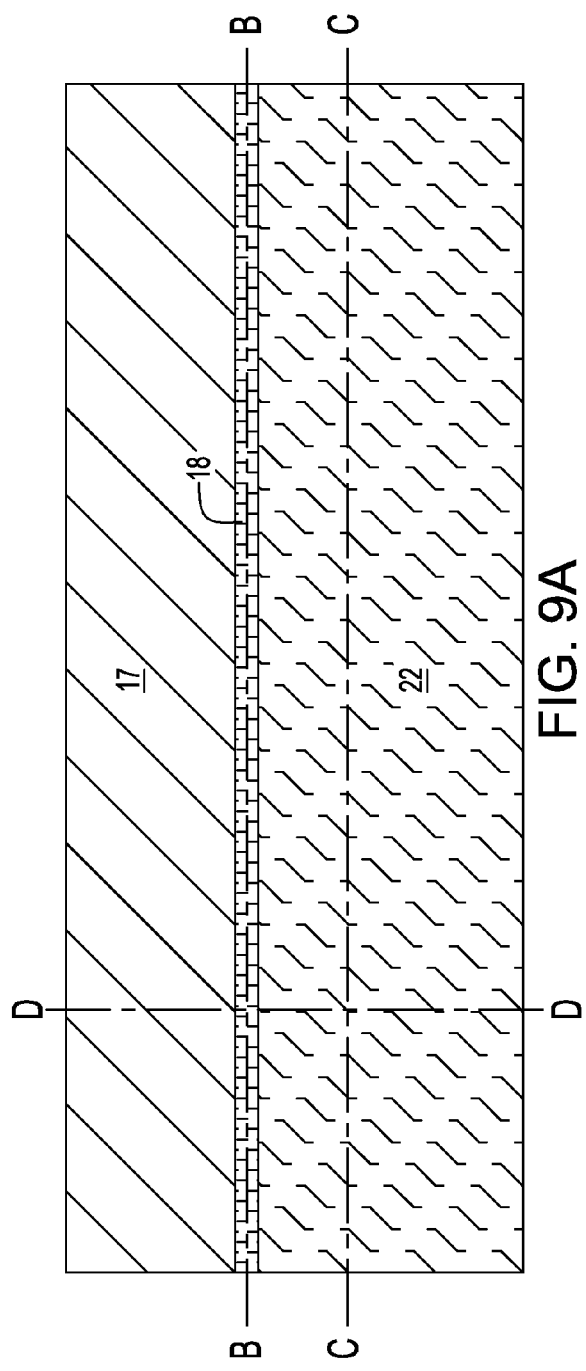
Figure 9B:
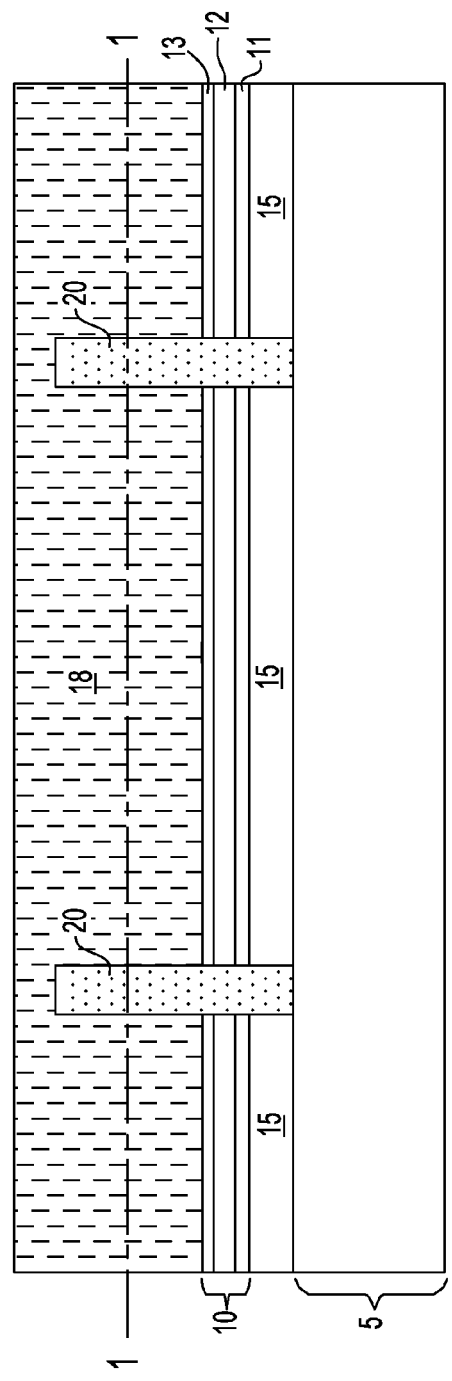
Figure 9E:
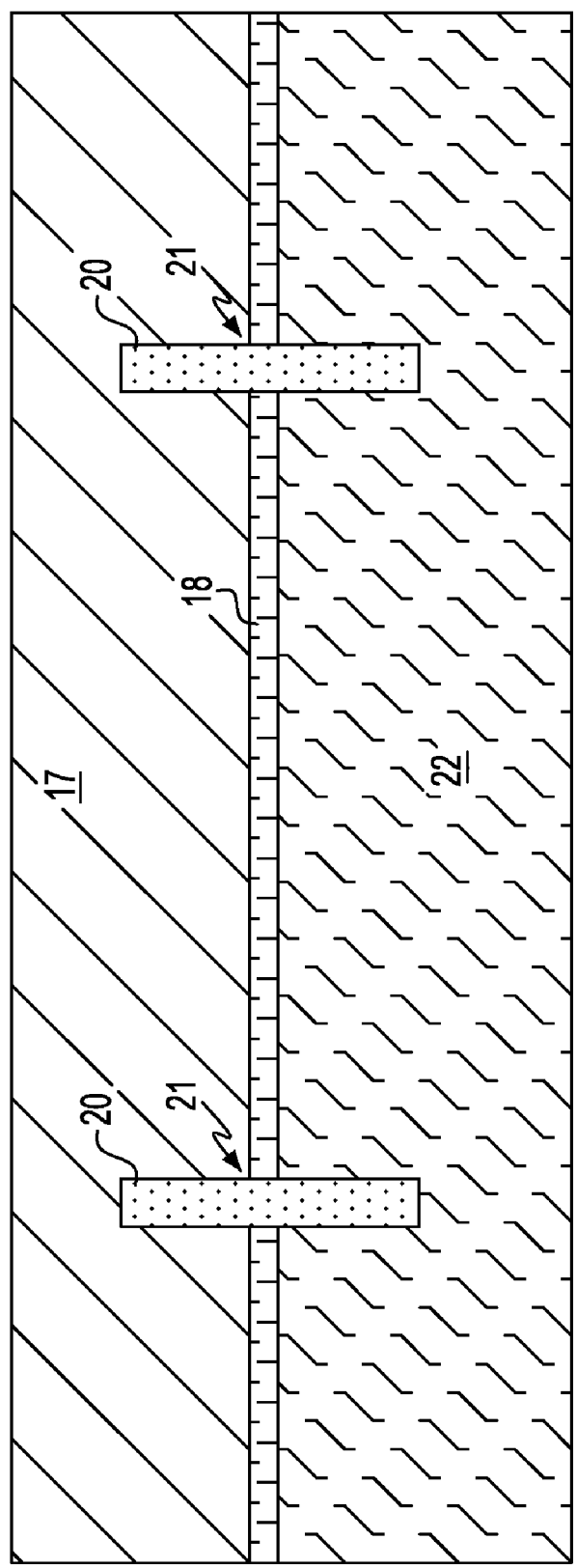
Figure 10C:
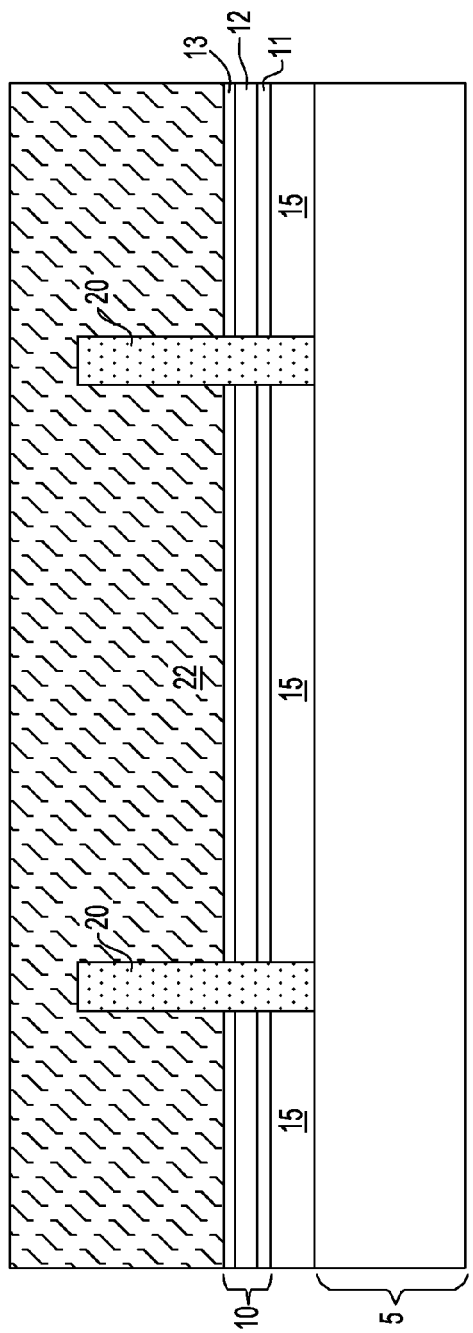
Figure 10D:
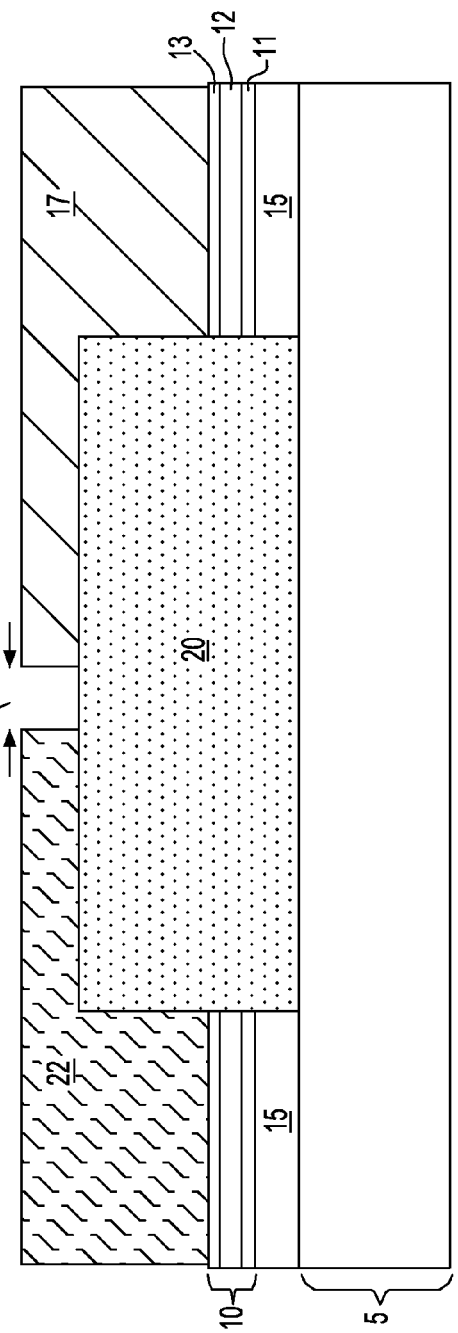

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. For purposes of the description hereinafter, the terms "upper", "lower", "right", "left", "vertical", "horizontal", "top", "bottom", and derivatives thereof shall relate to the invention, as it is oriented in the drawing figures. The terms "overlying", "atop", "positioned on" or "positioned atop" means that a first element, such as a first structure, is present on a second element, such as a second structure, wherein intervening elements, such as an interface structure, e.g. interface layer, may be present between the first element and the second element. The term "direct contact" means that a first element, such as a first structure, and a second element, such as a second structure, are connected without any intermediary conducting, insulating or semiconductor layers at the interface of the two elements.

In one embodiment, a method of forming nanopore is provided that includes forming a first structure having a first width of 5 nm or less and a first length of 10 nm or greater, and forming a second structure having a second width of 5 nm or less and a second length of 10 nm or greater, wherein an intersecting portion of the first and the second structures is etched to provide an opening having a width of 5 nm or less and a length of 5 nm or less. The opening provided by the etched intersecting portion of the first and second structures may be utilized as an etch mask for etching a substrate in providing a pore, such as a nanopore. The term "nanopore" denotes an opening having a diameter that is equal to 100 nm or less. It is not intended that the term "nanopore" be limited to circular geometries, as openings having multi-sided geometries are also suitable for providing a nanopore. A multi-sided opening having length and width dimensions that are equal to 5 nm or less may be referred to as a nanopore. Although the pore structures depicted in the supplied figures are formed through the entire thickness of the substrate, nanopores may also be provided that extend to only a partial depth of the substrate.

FIG. 1 illustrates one embodiment of a substrate 5 that is suitable for forming a nanopore array. The substrate 5 may include, but is not limited to, silicon containing materials, GaAs, InAs and other like semiconductors. Silicon containing materials as used to provide the substrate 5 include, but are not limited to, Si, bulk Si, single crystal Si, polycrystalline Si, SiGe, amorphous Si, silicon-on-insulator substrates (SOI), SiGe-on-insulator (SGOI), strained-silicon-on-insulator, annealed poly Si, and poly Si line structures. The substrate 5 may have a thickness ranging from 50 microns to 1000 microns. In another embodiment, the substrate 5 may have a thickness ranging from 200 microns nm to 700 microns. In yet another embodiment, the substrate 5 has a thickness ranging from 500 microns to 700 microns.

In one embodiment, a dielectric layer 15 may be present on an upper surface of the substrate 5. The dielectric layer 15 may be formed on the upper surface of the substrate 5 using deposition and/or growth processes. In one example, the dielectric layer 15 may be formed by a thermal growth process such as, for example, oxidation, nitridation or oxynitridation. In another example, the dielectric layer 15 can be formed by a deposition process such as, for example, chemical vapor deposition (CVD), plasma-assisted CVD, metal-organic chemical vapor deposition (MOCVD), atomic layer deposition (ALD), evaporation, reactive sputtering, chemical solution deposition and other like deposition processes.

The dielectric layer 15 may be composed of a dielectric material, including but not limited to, oxide, nitrides and oxynitrides. In one embodiment, the dielectric layer 15 may be selected from the group consisting of silicon containing materials such as $SiO_2$, $Si_3N_4$, $SiO_xN_y$, SiC, SiCO, SiCOH, and SiCH compounds; the above-mentioned silicon containing materials with some or all of the Si replaced by Ge; carbon-doped oxides; inorganic oxides; inorganic polymers; hybrid polymers; organic polymers such as polyamides or SiLK™; other carbon-containing materials; organo-inorganic materials such as spin-on glasses and silsesquioxane-based materials; and diamond-like carbon (DLC, also known as amorphous hydrogenated carbon, $\alpha$-C:H).

The dielectric layer 15 may have a thickness ranging from 10 nm to 100 nm. In another embodiment, the dielectric layer 15 may have a thickness ranging from 15 nm to 50 nm. In yet another embodiment, the dielectric layer 15 has a thickness ranging from 25 nm to 35 nm.

Still referring to FIG. 1, in one embodiment, a material stack 10 is formed on the upper surface of the substrate 5. In one example, the material stack 10 is a multi-layered structure that may provide the electrodes to the subsequently formed nanopores. The material stack 10 may include a first layer 11 composed of a first metal or a first metal nitride directly on the dielectric layer 15 that is present directly on the upper surface of the substrate 5, a second layer 12 composed of a dielectric on the first layer 11 of the first metal or the first melt nitride, and a third layer 13 composed of a second metal or a second metal nitride.

The first layer 11 may be composed of a metal, such as Ti, Al, Ta, Pt, W, Ag, Cu or alloys and multi-layers thereof, or a metal nitride, such as of WN, WSiN, TiN, TiSiN, TiAlN, TaN, TaSiN, TiTaN, TaRuN or combinations thereof. The first layer 11 may have a thickness ranging from 3 nm to 10 nm. In another embodiment, the first layer 11 has a thickness ranging from 5 nm to 7 nm.

The first layer 11 may be deposited using chemical vapor deposition (CVD) or physical vapor deposition (PVD). Chemical Vapor Deposition is a deposition process in which a deposited species is formed as a result of chemical reaction between gaseous reactants; wherein solid product of the reaction is deposited on the surface on which a film, coating, or layer of the solid product is to be formed. Variations of CVD processes include, but are not limited to, Atmospheric Pressure CVD (APCVD), Low Pressure CVD (LPCVD) and Plasma Enhanced CVD (EPCVD), Metal-Organic CVD (MOCVD), Atomic Layer Deposition (ALD) and others. Atomic layer deposition is a deposition form in which a monolayer, single layer, of atoms being deposited is formed from the gas precursors on the deposition surface. Atomic layer deposition may deposit multiple monolayers.

In another embodiment, the first layer 11 may be deposited using physical vapor deposition (PVD), such as sputtering. In one embodiment, in which the first layer 11 is a metal nitride, the sputtering deposition process for forming the first layer 11 includes applying high energy particles to strike a solid slab of a metal target material to provide the metal constituent of the metal nitride layer, such as titanium. The high energy particles physically dislodge metal atoms of target material, which are then deposited on the dielectric layer 15. The source of nitrogen for the metal nitride layer may be provided by nitrogen gas ($N_2$). The nitrogen source may be introduced to the sputtering chamber as the sputtered atoms of the metal constituent of the first layer 11 are migrating towards the deposition surface, e.g., the dielectric layer. In one embodiment, the first layer 11 is composed of TiN having a thickness ranging from 3 nm to 10 nm, which is deposited using sputtering.

The second layer 12 of the material stack 10 is typically a dielectric material. The dielectric material that provides the second layer 12 may be an oxide, nitride or oxynitride material. The dielectric material of the second layer 12 may be similar to the dielectric material of the dielectric layer 15. The second layer 12 may have a thickness ranging from 2 nm to 10 nm. In another embodiment, the second layer 12 has a thickness ranging from 3 nm to 5 nm. The second layer 11 may be deposited using chemical vapor deposition (CVD), such as atomic layer deposition. In one embodiment, the second layer 12 is composed of a high-k dielectric, such as aluminum oxide and hafnium oxide, having a thickness ranging from 3 nm to 5 nm, which is deposited using chemical vapor deposition or evaporation.

Similar to the first layer 11, the third layer 13 of the material stack 10 may be composed of a metal, such as Ti, Al, Ta, Pt, W, Ag, Cu or alloys and multi-layers thereof, or a metal nitride, such as of WN, WSiN, TiN, TiSiN, TiAlN, TaN, TaSiN, TiTaN, TaRuN or combinations thereof. The third layer 13 may have a thickness ranging from 3 nm to 10 nm. In another embodiment, the third layer 13 has a thickness ranging from 5 nm to 7 nm. It is noted that the methods described above for the first layer 11 of the material stack 10 are suitable for forming the third layer 13 of the material stack. In one embodiment, the third layer 13 is composed of TiN having a thickness ranging from 3 nm to 10 nm, which is deposited using sputtering.

FIG. 2 depicts one embodiment of forming a first pedestal 14 on the substrate 5. The first pedestal 14 may be formed atop the material stack 10 that is on the substrate 5 utilizing deposition, lithography and etching. More specifically, in one embodiment, a material layer for the first pedestal 14 may be provided atop the material stack 10 by blanket depositing a layer of material for the first pedestal 14, and then patterning and etching the material layer to provide the first pedestal 14. For example, forming the material layer for the first pedestal 14 may include blanket deposition of a semiconductor material, such as a silicon-containing semiconductor material, e.g., polysilicon. The blanket deposition for the material layer for the first pedestal 14 may be provided by chemical vapor deposition. Variations of CVD processes suitable for forming the material layer for the first pedestal 14 include, but are not limited to, Atmospheric Pressure CVD (APCVD), Low Pressure CVD (LPCVD) and Plasma Enhanced CVD (EPCVD), Metal-Organic CVD (MOCVD), Atomic Layer Deposition (ALD) and others. In one embodiment, the material layer for the first pedestal 14 has a thickness Ti of less than 1000 Å. In another embodiment, the material layer for the first pedestal 14 has a thickness Ti ranging from 100 Å to 1000 Å.

The material layer for the first pedestal 14 may be patterned using photolithography and etching. In one example, an etch mask may be formed atop the uppermost surface of the material layer for the first pedestal 14. In one embodiment, the etch mask may be provided by a patterned photoresist layer. The etch mask typically protects the portion of the material layer for the first pedestal 14 that provides the first pedestal 14, wherein the portions exposed by the etch mask are removed by an anisotropic etch process, such as a reactive ion etch. An anisotropic etch process is a material removal process in which the etch rate in the direction normal to the surface to be etched is higher than in the direction parallel to the surface to be etched. Reactive ion etch is a form of plasma etching, in which the surface to be etched is placed on the RF powered electrode and takes on a potential that accelerates an etching species, which is extracted from a plasma, towards the surface to be etched, wherein a chemical etching reaction takes place in the direction normal to the surface being etched. Following etch, the remaining portion of the material layer provides the first pedestal 14, in which the width W1 of the first pedestal 14 is selected to provide the pitch separating the nanopores. In another embodiment, the width W1 of the first pedestal 14 may range from 100 microns to 1000 microns. In yet another embodiment, the width W1 of the first pedestal 14 may range from 100 microns to 500 microns. It is noted that the width W1 is determined considering the width of the opening of the backside etch that is formed through the substrate 5.

FIG. 3 depicts one embodiment of forming a first sacrificial material 16 on sidewalls of the first pedestal 14. The first sacrificial material 16 may be formed in direct contact with the sidewalls of the first pedestal 14. The first sacrificial material 16 may be composed of a nitride, i.e., $Si_3N_4$, but may also comprise oxide or oxynitride materials. The first sacrificial material 16 may have a width W2 of less than 5 nm. In one embodiment, the first sacrificial material 16 may have a width W2 ranging from 2 nm to 5 nm. In yet another embodiment, the first sacrificial material 16 may have a width W2 of less than 2 nm. In one embodiment, the first sacrificial material 16 may have a length greater than 10 nm. In another embodiment, the first sacrificial material 16 may have a length ranging from 10 nm to 1000 nm. In yet another embodiment, the first sacrificial material 16 may have a length ranging from 100 nm to 300 nm.

The first sacrificial material 16 can be formed by deposition and etching. For example, a conformal dielectric layer may be deposited using deposition processes, including, but not limited to, chemical vapor deposition (CVD), plasma-assisted CVD, and low-pressure chemical vapor deposition (LPCVD). Following deposition, the conformal dielectric layer is then etched to define the geometry of the first sacrificial material 16 using an anisotropic plasma etch procedure such as, reactive ion etch. More specifically, in one embodiment, the forming of the first sacrificial material 16 on the sidewalls of the first pedestal 14 comprises conformal deposition of a first sacrificial material layer 16 on the sidewalls and upper surface of the first pedestal 14, and anisotropic etching of the first sacrificial material layer 16 so that a remaining portion of the first sacrificial material layer 16 is present on the sidewalls of the first pedestal 14.

FIG. 4 depicts one embodiment of forming a first mask 9 adjacent to the first sacrificial material 16. In one embodiment, the first mask 9 has an upper surface that is coplanar with an upper surface of the first pedestal 14. In one embodiment, the composition for the first mask 9 is selected to protect the underlying portion of the material stack 10.

The composition for the first mask 9 may be selected from the group consisting of silicon-containing or carbon-containing materials such as carbon, Si, $SiO_2$, $Si_3N_4$, $SiO_xN_y$, SiC, SiCO, SiCOH, and SiCH compounds, the above-mentioned silicon-containing materials with some or all of the Si replaced by Ge, carbon-doped oxides, inorganic oxides, inorganic polymers, hybrid polymers, organic polymers such as polyamides or SiLK™, other carbon-containing materials, organo-inorganic materials such as spin-on glasses and silsesquioxane-based materials, and diamond-like carbon (DLC, also known as amorphous hydrogenated carbon, $\alpha$-C:H). The first mask 9 may also be composed of a photoresist material. The first mask 9 may be formed by deposition processes, including, but not limited to spinning from solution, spraying from solution, chemical vapor deposition (CVD), plasma enhanced CVD (PECVD), sputter deposition, reactive sputter deposition, ion-beam deposition, and evaporation.

In one embodiment, the first mask 9 is planarized until the upper surface of the first mask 9 is coplanar with the upper surface of the first sacrificial material 16 and the upper surface of the first pedestal 14. Planarization is a material removal process that employs at least mechanical forces, such as frictional media, to produce a planar surface. One example of planarization is chemical mechanical planarization (CMP). Chemical mechanical planarization (CMP) is a material removal process using both chemical reactions and mechanical forces to remove material and planarize a surface. The planarization process typically exposes the upper surface of the first sacrificial material 16.

FIG. 5 depicts one embodiment of removing the first sacrificial material 16 to provide a first void 8 between the first pedestal 14 and the first mask 9. The first void 8 that is formed by removing the sacrificial material 16 has the dimensions of the sacrificial material 16. Therefore, when the first sacrificial material 16 has a width W2 of less than 5 nm, the first void 8 has a width W3 of less than 5 nm. In another embodiment, the first void 8 may have a width W3 ranging from 2 nm to 5 nm. In yet another embodiment, the first void 8 may have a width W3 of less than 2 nm. In one embodiment, the first void 8 may have a length greater than 10 nm. In another embodiment, the first void 8 may have a length ranging from 10 nm to 1000 nm. In yet another embodiment, the first void 8 may have a length ranging from 100 nm to 300 nm.

In one embodiment, removing the first sacrificial material 16 to provide a first void 8 between the first pedestal 14 and the first mask 9 includes etching the first sacrificial material 16 selective to the first pedestal 14 and the first mask 9. As used herein, the terms "selective" and "selectivity" in reference to a material removal process denotes that the rate of material removal for a first material is greater than the rate of removal for at least another material of the structure to which the material removal process is being applied. For example, in one embodiment, the selectivity for removing the first sacrificial material 16 to the first pedestal 14 and the first mask 9 is typically greater than 100. In one embodiment, the etch process that removes the first sacrificial material 16 is selective to the material stack 10 that is present on the substrate 5. The etch process may be an anisotropic etch, such as reactive ion etch (RIE).

FIG. 6 depicts etching the material stack 10 using the first void 8 as an etch mask. In one embodiment, the material stack 10 is etched using an etch chemistry that removes the material stack 10 selective to the first pedestal 14 and the first mask 9. In one example, a single etch process removes the first, second and third material layers 11, 12, 13 of the material stack 10 using a single etch chemistry that is selective to the first pedestal 14, the first mask 9 and the underlying dielectric layer 15. In another example, a separate etch chemistry is applied to etch each of the first, second and third material layers 11, 12, 13 of the material stack 10. In some examples, following etching of the material stack 10, the underlying dielectric layer 15 is etched to provide an opening exposing the upper surface of the substrate 5. In one embodiment, the material stack 10 is etched selectively to the substrate 5. The etch process for etching the material stack 10 and the dielectric layer 15 is typically an anisotropic etch, such as reactive ion etch (RIE). Because the first void 8 is used as an etch mask, the opening formed in the material stack 10 and the dielectric layer 15 has the same width and length dimensions as the first void 8.

FIGS. 7A and 7B depict filling the first void 8 to form a first structure 20 having a width W4 of 5 nm or less and a first length L4 of 10 nm or more. In one embodiment, the first structure 20 has a width W4 ranging from 2 nm to 5 nm. In yet another embodiment, the first structure 20 may have a width W4 of less than 2 nm. In one embodiment, the first structure 20 may have a length L4 greater than 10 nm. In another embodiment, the first structure 20 may have a length L4 ranging from 10 nm to 1000 nm. In yet another embodiment, the first structure 20 may have a length L4 ranging from 100 nm to 300 nm. The first structure 20 may be interchangeably referred to as a first nanostrip.

In one embodiment, the first void 8 is filled with a dielectric material. In one embodiment, the dielectric material is deposited to fill the first void 8 and extends onto the upper surface of the first mask 9 and the first pedestal 14. In one embodiment, the first void 8 is filled with a dielectric material using a deposition process, such as chemical vapor deposition. Variations of CVD processes suitable for filling the first void 8 include, but are not limited to, Atmospheric Pressure CVD (APCVD), Low Pressure CVD (LPCVD) and Plasma Enhanced CVD (EPCVD), Metal-Organic CVD (MOCVD) and others. In another embodiment, the first void 8 is filled with a dielectric deposited using spinning from solution, spraying from solution or a combination thereof.

The first structure 20 that is formed by filling the first void 8 may be composed of any dielectric including oxides, nitrides, oxynitrides or combinations and multi-layers thereof.

In some embodiments, the first structure 20 may be composed of $SiO_2$, $Si_3N_4$, SiON, $TiO_2$, $Al_2O_3$, $ZrO_2$, and other like oxides including perovskite-type oxides. The first structure 20 may also be composed of a high-k dielectric. A high-k dielectric may be a material having a dielectric constant that is greater than the dielectric constant of silicon oxide. In one embodiment, the high-k dielectric is comprised of a material having a dielectric constant that is greater than 4.0. Some examples of high-k dielectric materials suitable for the first structure 20 include hafnium oxide, hafnium silicon oxide, hafnium silicon oxynitride, lanthanum oxide, lanthanum aluminum oxide, zirconium oxide, zirconium silicon oxide, zirconium silicon oxynitride, tantalum oxide, titanium oxide, barium strontium titanium oxide, barium titanium oxide, strontium titanium oxide, yttrium oxide, aluminum oxide, lead scandium tantalum oxide, lead zinc niobate and combinations thereof. It is noted that the above noted materials are provided for illustrative purposes only, and that it is not intended that the present disclosure be limited to the above disclosed materials. Any material may be utilized for the first structure 20 so long as the material selected may be etched selectively to at least the subsequently formed second structure.

In one embodiment, a planarization process, such as chemical mechanical planarization (CMP), removes the portion of the material that fills the first void 8 from the upper surface of the first pedestal 14 and the first mask 9. In another embodiment, a selective etch process removes the portion of the material that fills the first void 8 from the upper surface of the first pedestal 14 and the first mask 9. The first mask 9 and the first pedestal 14 may be removed using an etch process that is selective to the first structure 20 and the material stack 10.

FIGS. 8A-8E depict forming a second pedestal 17 on the substrate 5, wherein the second pedestal 17 is formed over a first end 19 of the first structure 20. The first end 19 of the first structure 20 that is under the second pedestal 17 is depicted by the broken line identified by reference number 19 in FIG. 8A. The second pedestal 17 is formed atop the material stack 10 that is on the substrate 5 utilizing deposition, lithography and etching processes. Similar to the first pedestal 14, the second pedestal 17 may be formed by depositing a semiconductor material, such as a silicon-containing semiconductor material, e.g., polysilicon, and then patterning the semiconductor material using photolithography and etching. The details of one embodiment of a process for forming the second pedestal 17 are described above with reference to FIG. 2.

FIGS. 8A-8E depict forming a second structure 18 on the sidewall of the second pedestal 17. The second structure 18 can be formed by deposition and etch processes. For example, a conformal dielectric layer for the second structure 18 may be deposited using deposition processes, including, but not limited to, chemical vapor deposition (CVD), plasma-assisted CVD, and low-pressure chemical vapor deposition (LPCVD). Following deposition, the conformal dielectric layer is then etched to define the geometry of the second structure 18 using an anisotropic plasma etch procedure such as, reactive ion etch.

The second structure 18 may be composed of any dielectric including oxides, nitrides, oxynitrides or combinations and multi-layers thereof. In some embodiments, the second structure 18 may be composed of $SiO_2$, $Si_3N_4$, SiON, $TiO_2$, $Al_2O_3$, $ZrO_2$, and other like oxides including perovskite-type oxides.

The second structure 18 may also be composed of a high-k dielectric. Some examples of high-k dielectric materials suitable for the second structure 18 include hafnium oxide, hafnium silicon oxide, hafnium silicon oxynitride, lanthanum oxide, lanthanum aluminum oxide, zirconium oxide, zirconium silicon oxide, zirconium silicon oxynitride, tantalum oxide, titanium oxide, barium strontium titanium oxide, barium titanium oxide, strontium titanium oxide, yttrium oxide, aluminum oxide, lead scandium tantalum oxide, lead zinc niobate and combinations thereof. It is noted that the above noted materials are provided for illustrative purposes only, and that it is not intended that the present disclosure be limited to the above disclosed materials.

Any material may be utilized for the second structure 18 so long as the material selected may be etched selectively to at least the first structure 20. For example, when the first structure 20 is composed of silicon nitride ($Si_3N_4$), the second structure 18 may be composed of silicon oxide ($SiO_2$). In another example, in which the first structure 20 is composed of silicon oxide ($SiO_2$), the first structure 20 is composed of silicon nitride ($Si_3N_4$).

In one embodiment, the length L5 of the second structure 18 is substantially perpendicular to the length L4 of the first structure 20. By "substantially perpendicular" it is meant that the angle α1 defined by the sidewalls of the first structure 20 and the second structure 18 at the intersecting portion 21 of the first structure 20 is equal to 90° plus or minus 25°. In one embodiment, the angle α1 defined by the sidewalls of the first structure 20 and the second structure 18 is equal to 90° plus or minus 15°. In another embodiment, the angle α1 defined by the sidewalls of the first structure 20 and the second structure 18 is equal to 90°. Although the second structure 18 is depicted as a single structure, the second structure 18 may be included as multiple separate portions, so long as at least one portion of the second structure 18 is overlapping the intersecting portion 21 of the first structure 20. The intersecting portion 21 of the first structure 20 has a first width of 5 nm or less and an exposed length of 5 nm or less.

The second structure 18 may be composed of an oxide, i.e., $SiO_2$, but may also comprise nitride or oxynitride materials. The second structure 18 may have a width W5 of less than 5 nm. In one embodiment, the second structure 18 may have a width W5 ranging from 2 nm to 5 nm. In yet another embodiment, the second structure 18 may have a width W5 of less than 2 nm. In one embodiment, the second structure 18 may have a length L5 greater than 10 nm. In another embodiment, the second structure 18 may have a length L5 ranging from 10 nm to 1000 nm. In yet another embodiment, the second structure 18 may have a length L5 ranging from 100 nm to 300 nm.

FIGS. 9A-9E depict forming a second mask 22 adjacent to the second structure 18. The second mask 22 that is depicted in FIGS. 9A-9E is similar to the first mask 9 that is described above with reference to FIG. 4. In one embodiment, the second mask 22 has an upper surface that is coplanar with an upper surface of the first pedestal 14. The composition for the second mask 22 is selected to protect the underlying portion of the material stack 10 during the later process sequences that include selective etching.

FIGS. 10A-10D depict one embodiment of etching the second structure 18 to expose the intersecting portion 21 of the first structure 20. The second structure 18 may be etched with an anisotropic etch that is selective to at least the second mask 22, and the second pedestal 17. In one embodiment, the anisotropic etch process is a reactive ion etch (RIE) process. In one example, the anisotropic etch is timed to terminate on the intersecting portion 21 of the first structure 20. In another example, the anisotropic etch is terminated on the intersecting portion 21 of the first structure 20 using end point detection. In yet another example, the anisotropic etch may remove the second structure 18 selectively to the first structure 20. In one example, in which the first structure 20 is composed of silicon nitride ($Si_3N_4$), the second structure 18 is composed of silicon oxide $SiO_2$, the etch chemistry that exposes the intersecting portion 21 of the first structure 20 is composed of $CHF_3$ and $O_2$. In this example, the selectivity of the etch for removing the silicon oxide ($SiO_2$) selectively to silicon nitride ($Si_3N_4$) ranges from 7:1 to 20:1.

The exposed intersecting portion 21 of the first structure 20 may have a length L7 of 5 nm or less than and a width W7 of 5 nm or less. In one embodiment, the exposed intersecting portion 21 of the first structure 20 may have a length L7 that ranges from 1 nm to 5 nm, and the intersecting portion 21 of the first structure 20 may have a width W7 that ranges from 1 nm to 5 nm. In yet another embodiment, the exposed intersecting portion 21 of the first structure 20 may have a length L7 of 2 nm or less than, and a width W7 of 2 nm or less. In one example, the exposed intersecting portion 21 of the first structure 20 may have a length L7 of 2 nm, and a width W7 of 2 nm.

FIGS. 11A-11B depict one embodiment of etching the exposed intersecting portion 21 of the first structure 20 to provide an opening 30 having a width of 5 nm or less and a length of 5 nm or less. The exposed intersecting portion 21 of the first structure 20 may be etched with an anisotropic etch that is selective to at least the second structure 18, the second mask 22, the second pedestal 17, and the semiconductor substrate 5. In one embodiment, the anisotropic etch process is a reactive ion etch (RIE) process. In another example, the anisotropic etch is terminated on the substrate 5 using end point detection. In one example, in which the exposed intersecting portion 21 of the first structure 20 is composed of silicon nitride ($Si_3N_4$), the second structure 18 is composed of silicon oxide ($SiO_2$), the etch that removes the intersecting portion 21 of the first structure 20 is a reactive ion etch composed of $CHF_3$ and $O_2$. In this example, the selectivity of the etch for removing the silicon nitride ($Si_3N_4$) exposed intersecting structure to the remaining portion of the silicon oxide ($SiO_2$) second structure 18 ranges from 7:1 to 20:1. In another example, in which the exposed intersecting portion 21 of the first structure 20 is composed of silicon nitride ($Si_3N_4$), the second structure 18 is composed of silicon oxide ($SiO_2$), the etch that removes the intersecting portion 21 of the first structure 20 is composed of a wet chemistry of hot phosphoric acid. In this example, the selectivity of the etch for removing the silicon nitride ($Si_3N_4$) exposed intersecting portion 21 of the first structure 20 to the remaining portion of the silicon oxide ($SiO_2$) second structure 18 is greater than 100:1.

FIGS. 12A-12D depict etching the substrate 5. In this embodiment, the length and width dimensions of the nanopore 35 are dictated by the opening through the second mask 22, the second pedestal 17, the second structure 18, the material stack 10 and the dielectric layer 15, wherein the substrate 5 is opened to the nanopore 35b using a backside substrate etch. In one embodiment, the backside substrate etch removes the substrate 5 selective to the dielectric layer 15. In one example, an etch mask (not shown) may be formed atop the backside surface of the substrate 5. In one embodiment, the etch mask may be provided by a patterned photoresist layer. The etch mask typically exposes the portion of the substrate 5 that is aligned to the nanopore 35. The exposed portion of the substrate 5 is then etched by an etch process that is selective to the dielectric layer opening the substrate 5 to the nanopore 35. Following etch, the remaining portion of the material layer provides the first pedestal 14, in which the width W1 of the first pedestal 14 is selected to provide the pitch separating the nanopores. In some embodiments, the opening that is formed through the substrate 5 by the backside etch has a greater width at the backside surface of the substrate than the portion of the substrate that is adjacent to the nanopore 35. In one embodiment, the width of the opening at the backside surface of the substrate 5 may range from 100 microns to 900 microns. In yet another embodiment, the width of the opening at the backside surface of the substrate 5 may range from 200 microns to 700 microns. Although FIGS. 1-12D depict a structure having only two nanopores 35 the present disclosure can form any number of nanopores 35. For example, in one embodiment, an array of nanopores 35 may be provided by the present method.

Figure 13:
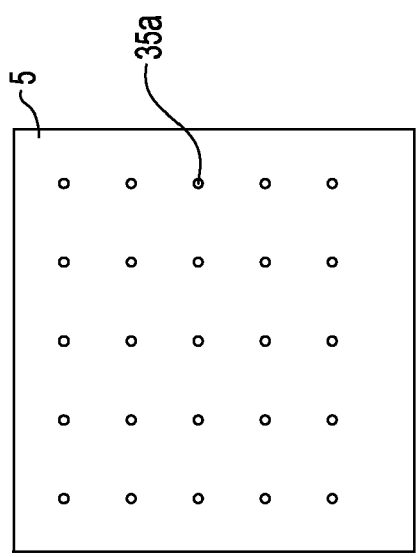
FIG. 13 is a top down planar view of an array of nanopores formed through a substrate, in accordance with one embodiment of the present disclosure.

FIG. 13 depicts an array of nanopores 35 formed through a substrate 5. The term "array" denotes a plurality of trapezoid shaped pores 35. In one embodiment, the array of nanopores 35 includes a concentration of nanopores 35 that ranges from 100 pores/$cm^3$ to $1 \times 10^{10}$ pores/$cm^3$. In another embodiment, the array of nanopores 35 includes a concentration of nanopores 35 that ranges from 10000 pores/$cm^3$ to $1 \times 10^6$ pores/$cm^3$. In yet another embodiment, the array of trapezoid shaped pores 35 includes a concentration of trapezoid shaped pores 35 that ranges from 10 pores/$cm^3$ to 100 pores/$cm^3$.

In one embodiment, the standard deviation of the width W8 of the nanopore 35 ranges from 1 to 10. In another embodiment, the standard deviation of the width W8 of the nanopore 35 ranges from 1 to 5. In yet another embodiment, the standard deviation of the width W8 of nanopore 35 ranges from 1 to 3. In one embodiment, the standard deviation of the length L8 of the nanopore 35 ranges from 1 to 10. In another embodiment, the standard deviation of the length L8 of the nanopore 35 ranges from 1 to 5.

Figure 14:
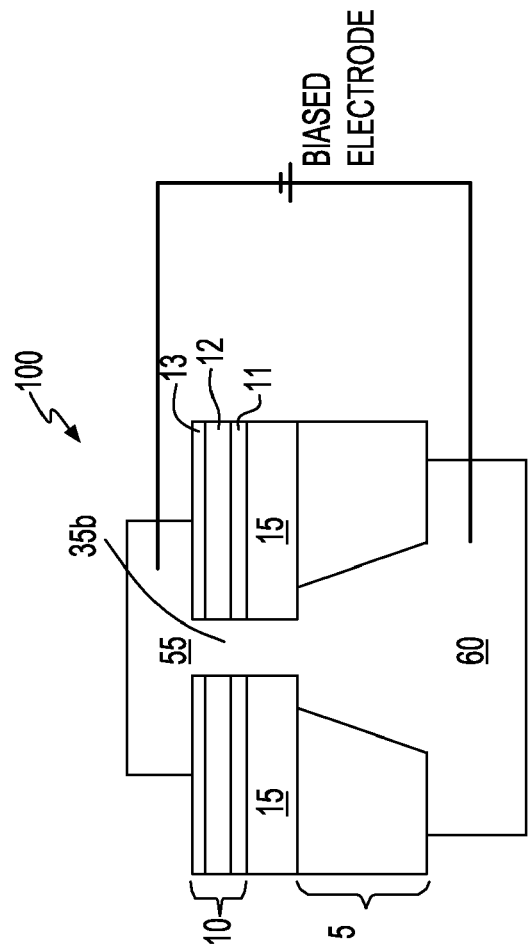
FIG. 14 depicts one embodiment of a nanopore array being utilized as a fluidic channel, in accordance with another embodiment of the present disclosure.

FIG. 14 depicts one embodiment of a nanopore 35 being utilized as a fluidic channel 100. The fluidic channel 100 of the present disclosure may be employed in DNA sequencing, molecular sensors, molecular filters and water treatment. FIG. 15 depicts one embodiment of a fluidic channel 100 being utilized to provide a molecular solution. Reference number 55 depicts a DNA solution in salt with a concentration gradient. The concentration is typically equal to approximately 500 nM. Reference number 60 depicts a salt solution. The salt solution 60 is typically composed of 1M KCl/10 nM Tris.Cl. The PH of the solution 60 is approximately 8.5. In one embodiment, DNA from the DNA solution in salt 55 translocate through the nanopore 35. A bias is applied to the structure depicted in FIG. 14 to control the translocation rate. The above noted applications for the fluidic channel 100 are provided for illustrative purposes, and are not intended to limit the application of the methods and structures disclosed in the present disclosure.

While this invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A method of forming a pore comprising;
  forming a first structure on a substrate;
  forming a second structure on the substrate, wherein the second structure is present on an intersecting portion of the first structure;
  forming an etch mask over exposed portions of the first structure and exposed portions of the substrate;

first etching the second structure selective to the etch mask, wherein the first etching exposes the intersecting portion of the first structure, wherein a remaining portion of the second structure is present on opposing sides of the intersecting portion of the first structure;

second etching the intersecting portion of the first structure selective to the etch mask and the remaining portion of the second structure to provide an opening to the substrate; and extending the opening through the substrate to provide a nanopore.

2. The method of claim 1, wherein the first structure has a first width of 5 nm or less and a first length of 10 nm or greater, the second structure has a second width of 5 nm or less and a second length that is 10 nm or greater, the intersection portion of the first structure having the first width of 5 nm or less and an exposed length of 5 nm or less, and the opening to the substrate has the first width of 5 nm or less and the exposed length of 5 nm or less.

3. The method of claim 2, wherein the first width of the first structure is equal to 2 nm or less, and the second width of the second structure is equal to 2 nm or less, wherein the second length of the second structure is substantially perpendicular to the first length of the first structure.

4. The method of claim 2 further comprising a material stack present on the upper surface of the substrate, the material stack comprising a first layer composed of a first metal or a first metal nitride on the upper surface of the substrate, a second layer composed of a dielectric on the first layer of the first metal or the first melt nitride, and a third layer composed of a second metal or a second metal nitride.

5. The method of claim 4, wherein the forming of the first structure comprises forming a first pedestal on the material stack of the substrate;

forming a first sacrificial material on sidewalls of the first pedestal; and forming a first hard mask having an upper surface coplanar with an upper surface of the first pedestal and the first sacrificial material;

removing the first sacrificial material to provide a void adjacent to the first pedestal;

removing the portion of the material stack exposed by the void to expose the upper surface of the substrate;

filling the second void to form the first structure, wherein the first structure contacts the upper surface of the substrate within the second void; and removing the first pedestal and the first hard mask.

6. The method of claim 5, wherein forming the second structure comprises:

forming a second pedestal on the substrate, wherein the second pedestal overlaps a first end of the first structure;

forming the second structure on sidewalls of the second pedestal, wherein the second structure overlaps a portion of the first structure between the first end and a second end of the first structure; and forming a second hard mask having an upper surface coplanar with an upper surface of the second pedestal and the second structure, wherein the second hard mask is present over the second end of the first structure.

7. The method of claim 5, wherein the etch mask is provided by the second pedestal and the second hard mask, and wherein the first etching the second structure selective to the etch mask to expose the intersecting portion of the first structure comprises an anisotropic etch.

8. The method of claim 7, wherein the first etching is timed to terminate on the intersecting portion of the first structure or the first etching is terminated using end point detection to expose the intersecting portion of the first structure.

9. The method of claim 7, wherein the second etching of the intersecting portion of the first structure selective to the etch mask and the remaining portion of the second structure to provide the opening to the substrate further comprises removing the intersecting portion of the first structure selective to the material stack and removing the material stack selective to the substrate.

10. A method of forming a pore comprising:

forming a first structure on a substrate;

forming a first mask structure on the substrate and over a first end portion of the first structure;

forming a second mask structure on the substrate adjacent and over a second end portion of the first structure;

forming a second structure between the first mask structure and the second mask structure, the second structure overlapping the first structure;

etching the second structure with an etch selective to the first mask structure and the second mask structure to provide an exposed intersecting portion of the first structure; and etching the exposed intersecting portion of the first structure to provide an opening.

11. The method of claim 10, wherein the first structure has a first width of 5 nm or less and a first length of 10 nm or more, the second structure having a second width of 5 nm or less and a second length of 10 nm or greater, the exposed intersecting portion of the first structure having an exposed first width of 5 nm or less and an exposed first length of 5 nm or less, and the opening having the exposed first length of 5 nm or less and the exposed first width of 5 nm or less.

12. The method of claim 11, wherein the second length of the second structure is substantially perpendicular to the first length of the first structure.

13. The method of claim 12, further comprising extending the opening through the substrate.

14. The method of claim 11, further comprising a material stack present on the upper surface of the substrate, the material stack comprising a first layer composed of a first metal or a first metal nitride on the upper surface of the substrate, a second layer composed of a dielectric on the first layer of the first metal or the first melt nitride, and a third layer composed of a second metal or a second metal nitride.

15. The method of claim 11, wherein the forming of the first structure comprises:

forming a first pedestal on the substrate;

forming a first sacrificial material on sidewalls of the first pedestal, wherein the sacrificial material has a width of 5 nm or less and a length of 10 nm or greater; and forming a first hard mask having an upper surface coplanar with an upper surface of the first pedestal and the first sacrificial material;

removing the first sacrificial material to provide a void adjacent to the first pedestal;

filling the second void to form a first structure; and removing the first pedestal and the first hard mask with an etch that is selective to the first structure.

16. The method of claim 15, wherein forming the first pedestal comprises:

depositing a layer of a first pedestal dielectric layer on the substrate;

forming a first etch mask on the first pedestal dielectric layer; and etching the layer of the first pedestal dielectric layer gate stack selective to the first etch mask to provide the first pedestal.

17. The method of claim 16, wherein the forming of the first sacrificial material on the sidewalls of the first pedestal comprises conformal deposition of a first sacrificial material layer on the sidewalls and upper surface of the first pedestal, and anisotropic etching of the first sacrificial material layer so that a remaining portion of the first sacrificial material layer is present on the sidewalls of the first pedestal and provides the first sacrificial material.

18. The method of claim 12, wherein the forming of the first mask structure, the forming of the second mask structure, and the forming of the second structure comprises:
    forming a second pedestal on the substrate, wherein the second pedestal overlaps a first end of the first structure, wherein the second pedestal provides the first mask;
    forming the second structure on sidewalls of the second pedestal, wherein the second sacrificial material have the second width of 5 nm or less and the second length of 10 nm or greater, wherein the second length of the second sacrificial material is perpendicular to the first length of the first structure, and overlaps a portion of the first structure between the first end and the second end of the first structure; and
    forming a second hard mask having an upper surface coplanar with an upper surface of the second pedestal and the second structure, wherein the second hard mask provides the second hard mask structure and is present over the second end of the first structure.

19. A method of forming a pore comprising:
    forming a first sacrificial material on sidewalls of a first pedestal that is present on a substrate;
    forming a first hardmask adjacent to the first sacrificial material;
    removing the first sacrificial material to provide a first void between the first pedestal structure and the first hardmask;
    forming a first structure filling the first void;
    removing the first pedestal and the first hardmask selective to the first structure;
    forming a second pedestal on the substrate, wherein the second pedestal overlaps an intersecting portion of the first structure;
    forming a second structure on sidewalls of the second pedestal and on a first end portion of the first structure;
    forming a second mask adjacent to the second structure, wherein the second mask is present over a second end portion of the first structure;
    etching the second structure to expose the intersecting portion of the first structure, wherein a remaining portion of the second structure is present on opposing sides of the first structure;
    etching the intersecting portion of the first structure selective to the second structure, the second mask and the second pedestal to provide a nanopore; and
    etching the substrate with a backside etch to expose the nanopore.

20. The method of claim 19, wherein a first structure filling the first void, wherein the first structure has a first width of 5 nm or less and a first length of 10 nm or more, wherein the second structure has a second width of 5 nm or less and a second length of 10 nm or more, and the opening has a length of 5 nm or less than and a width of 5 nm or less.

* * * * *